US009073873B2

(12) United States Patent
Hinman et al.

(10) Patent No.: US 9,073,873 B2
(45) Date of Patent: Jul. 7, 2015

(54) 2-HETEROCYCLYLAMINOALKYL-(P-QUINONE) DERIVATIVES FOR TREATMENT OF OXIDATIVE STRESS DISEASES

(71) Applicant: Edison Pharmaceuticals, Inc., Mountain View, CA (US)

(72) Inventors: Andrew W. Hinman, San Francisco, CA (US); Orion D. Jankowski, Burlingame, CA (US); Kieron E. Wesson, Burlingame, CA (US)

(73) Assignee: Edison Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 14/223,932

(22) Filed: Mar. 24, 2014

(65) Prior Publication Data
US 2014/0323509 A1   Oct. 30, 2014

Related U.S. Application Data

(62) Division of application No. 12/997,869, filed as application No. PCT/US2009/048308 on Jun. 23, 2009, now Pat. No. 8,716,486.

(60) Provisional application No. 61/133,169, filed on Jun. 25, 2008.

(51) Int. Cl.
| C07C 50/04 | (2006.01) |
| C07D 239/50 | (2006.01) |
| A61K 31/22 | (2006.01) |
| A61K 31/505 | (2006.01) |
| A61P 3/10 | (2006.01) |
| A61P 25/16 | (2006.01) |
| A61P 25/14 | (2006.01) |
| A61P 25/00 | (2006.01) |
| C07D 239/42 | (2006.01) |
| C07D 213/74 | (2006.01) |

(52) U.S. Cl.
CPC ............. *C07D 239/42* (2013.01); *A61K 31/22* (2013.01); *A61K 31/505* (2013.01); *C07C 50/04* (2013.01); *C07D 213/74* (2013.01)

(58) Field of Classification Search
CPC ...... C07C 50/04; C07D 239/50; A61K 31/22; A61K 31/505
USPC ........... 552/307; 568/626; 544/322; 514/454, 514/455, 690, 275
See application file for complete search history.

(56) References Cited

U.S. PATENT DOCUMENTS

| 5,801,159 | A | 9/1998 | Miller et al. |
| 6,232,060 | B1 | 5/2001 | Miller et al. |
| 6,426,362 | B1 | 7/2002 | Miller et al. |
| 6,528,042 | B1 | 3/2003 | Brown et al. |
| 6,608,196 | B2 | 8/2003 | Wang et al. |
| 6,653,346 | B1 | 11/2003 | Wang et al. |
| 7,034,054 | B2 | 4/2006 | Miller et al. |
| 7,078,541 | B2 | 7/2006 | Boddupalli et al. |
| 7,119,117 | B2 | 10/2006 | Beinlich et al. |
| 7,179,928 | B2 | 2/2007 | Smith et al. |
| 7,393,662 | B2 | 7/2008 | Heavner et al. |
| 7,432,305 | B2 | 10/2008 | Miller et al. |
| 7,470,798 | B2 | 12/2008 | Wang et al. |
| 7,491,312 | B2 | 2/2009 | Gilat et al. |
| 7,514,461 | B2 | 4/2009 | Wang et al. |
| 7,718,176 | B2 | 5/2010 | Heavner et al. |
| 7,875,607 | B2 | 1/2011 | Wang et al. |
| 7,968,746 | B2 | 6/2011 | Jankowski et al. |
| 8,044,097 | B2 | 10/2011 | Wang et al. |
| 8,106,223 | B2 | 1/2012 | Wesson et al. |
| 8,314,153 | B2 | 11/2012 | Miller et al. |
| 8,716,486 | B2 * | 5/2014 | Hinman et al. ............ 546/289 |
| 2002/0132845 | A1 | 9/2002 | Miller et al. |
| 2003/0022818 | A1 | 1/2003 | Miller et al. |
| 2003/0144219 | A1 | 7/2003 | Phinney et al. |
| 2005/0065099 | A1 | 3/2005 | Walkinshaw et al. |
| 2005/0067303 | A1 | 3/2005 | Wong et al. |
| 2006/0281809 | A1 | 12/2006 | Miller et al. |
| 2007/0225261 | A1 | 9/2007 | Miller et al. |
| 2007/0260076 | A1 | 11/2007 | Lipshutz et al. |
| 2009/0162890 | A1 | 6/2009 | Gilat et al. |
| 2009/0163529 | A1 | 6/2009 | Gilat et al. |
| 2009/0291092 | A1 | 11/2009 | Miller et al. |

(Continued)

FOREIGN PATENT DOCUMENTS

| JP | 58-83698 A | 5/1983 |
| JP | 62-223150 A | 10/1987 |

(Continued)

OTHER PUBLICATIONS

Barbiroli, B. et al. (1995). "Lipoic (Thioctic) Acid Increases Brain Energy Availability and Skeletal Muscle Performance as Shown by In Vivo $^{31}$P-MRS in a Patient with Mitochondrial Cytopathy," *J Neurol.* 2412(7):472-477.

Bennet, J.C. et al. Ed. (1996) *Cecil Textbook of Medicine*, 20th Edition, vol. 1, 1004-1010.

Cadenas, E. et al. (2000). "Mitochondrial Free Radical Generation, Oxidative Stress and Aging," *Free Radical Biology & Medicine* 29(3/4):222-230.

Catarina, et al. (Jun. 2010) *Dev. Disabil. Res. Rev.* 162(2):183-188.

Chariot, P. et al. (Apr. 1994). "Determination of the Blood Lactate:Pyruvate Ratio As a Noninvasive Test for the Diagnosis of Zidovudine Myopathy," *Arthritis & Rheumatism* 37(4):583-586.

(Continued)

*Primary Examiner* — Venkataraman Balasubramanian
(74) *Attorney, Agent, or Firm* — Squire Patton Boggs (US) LLP

(57) ABSTRACT

Methods of treating or suppressing oxidative stress disorders including mitochondrial diseases, impaired energy processing disorders, neurodegenerative diseases and diseases of aging are disclosed, as well as compounds useful in the methods of the invention, such as 2-heterocyclylaminoalkyl-(p-quinone) derivatives.

17 Claims, No Drawings

(56) References Cited

U.S. PATENT DOCUMENTS

| | | |
|---|---|---|
| 2010/0010100 A1 | 1/2010 | Hinman et al. |
| 2010/0029784 A1 | 2/2010 | Hinman et al. |
| 2010/0056429 A1 | 3/2010 | Miller et al. |
| 2010/0222436 A1 | 9/2010 | Miller et al. |
| 2010/0249032 A1 | 9/2010 | Heavner et al. |
| 2010/0266591 A1 | 10/2010 | Bugelski et al. |
| 2010/0273892 A1 | 10/2010 | Miller et al. |
| 2010/0273894 A1 | 10/2010 | Miller |
| 2011/0046156 A1 | 2/2011 | Miller |
| 2011/0046219 A1 | 2/2011 | Hiinman et al. |
| 2011/0124679 A1 | 5/2011 | Hinman et al. |
| 2011/0142834 A1 | 6/2011 | Miller |
| 2011/0172312 A1 | 7/2011 | Miller et al. |
| 2011/0207828 A1 | 8/2011 | Miller et al. |
| 2011/0269776 A1 | 11/2011 | Miller |
| 2012/0088783 A1 | 4/2012 | Wang et al. |
| 2012/0101169 A1 | 4/2012 | Hawi |
| 2012/0122934 A1 | 5/2012 | Jankowski et al. |
| 2012/0122969 A1 | 5/2012 | Miller |
| 2012/0130093 A1 | 5/2012 | Wesson et al. |
| 2012/0136048 A1 | 5/2012 | Miller et al. |
| 2012/0295985 A1 | 11/2012 | Miller et al. |
| 2013/0053450 A1 | 2/2013 | Miller et al. |
| 2013/0109759 A1 | 5/2013 | Miller |
| 2013/0116336 A1 | 5/2013 | Shrader |

FOREIGN PATENT DOCUMENTS

| | | |
|---|---|---|
| JP | 2007-515408 A | 6/2007 |
| JP | 2009-527567 A | 7/2009 |
| WO | WO-03/064403 A1 | 8/2003 |
| WO | WO-2004/003565 A2 | 1/2004 |
| WO | WO-2004/003565 A3 | 1/2004 |
| WO | WO-2005/056812 A2 | 6/2005 |
| WO | WO-2005/056812 A3 | 6/2005 |
| WO | WO-2007/100652 A2 | 9/2007 |
| WO | WO-2007/100652 A3 | 9/2007 |
| WO | WO-2011/041452 A2 | 4/2011 |
| WO | WO-2011/113018 A1 | 9/2011 |
| WO | WO-2012/019029 A2 | 2/2012 |
| WO | WO-2012/019029 A3 | 2/2012 |
| WO | WO-2012/019032 A1 | 2/2012 |
| WO | WO-2012/154613 A1 | 11/2012 |
| WO | WO-2012/170773 A1 | 12/2012 |
| WO | WO-2012/174286 A1 | 12/2012 |
| WO | WO-2013/006736 A1 | 1/2013 |
| WO | WO-2013/006737 A1 | 1/2013 |
| WO | WO-2013/013078 A1 | 1/2013 |

OTHER PUBLICATIONS

Chariot, P. et al. (Jul. 1994). "Optimal Handling of Blood Samples for Routine Measurement of Lactate and Pyruvate," *Arch. Pathol. Lab. Med.* 118(7):695-697.

Dermer et al. (1994) Bio/Technology, 12:320.

Deschauer, M. et al. (2005). "A Novel *ANT1* Gene Mutation with Probable Germline Mosaicism in Autosomal Dominant Progressive External Ophthalmoplegia," *Neuromuscular Disorders* 15:311-315.

Dimauro, S. (1999). "Exercise Intolerance and the Mitochondrial Respiratory Chain," *Ital. J. Neurol. Sci.* 20:387-393.

Erhola, M. et al. (1997). "Biomarker Evidence of DNA Oxidation in Lung Cancer Patients: Association of Urinary 8-Hydroxy-2'-Deoxyguanosine Excretion with Radiotherapy, Chemotherapy, and Response to Treatment," *FEBS Letters* 409(2):287-291.

Fabrizi, G.M. et al. (1996). "Autosomal Dominant Limb Girdle Myopathy with Ragged-Red Fibers and Cardiomyopathy. A Pedigree Study by In Vivo $^{31}$P-MR Spectroscopy Indicating a Multisystem Mitochondrial Defect," *Journal of the Neurological Sciences* 137(1):20-27.

Freshney et al. (1983). *Culture of Animal Cells, A Manual of Basic Technique*, Alan R. Liss, Inc., New York, New York, , p. 4.

Gempel, K. et al. (2007). "The Myopathic Form of Coenzyme Q10 Deficiency is Caused by Mutations in the Electron-Transferring-Flavoprotein Dehydrogenase (*ETFDH*) Gene," *Brain* 130(8):2037-2044.

Golub et al. (1999). *Science*, 286, pp. 531-537.

Gottlieb, H.E. et. al. (1997). "NMR Chemical Shifts of Common Laboratory Solvents as Trace Impurities," *J. Org. Chem.* 62:7512-7515.

Harman, D. (Jul. 1956). "Aging: A Theory Based on Free Radical and Radiation Chemistry," *Journal of Gerontology* 11(3):298-300.

Honda, M. et al. (2000). "Correlation of Urinary 8-Hydroxy-2'-Deoxyguanosine (8-OHdG), a Biomarker of Oxidative DNA Damage, and Clinical Features of Hematological Disorders: A Pilot Study," *Leukemia Research* 24(6):461-468.

Jauslin, M.L. et al. (2002). "A Cellular Model for Friedreich Ataxia Reveals Small-Molecule Glutathione Peroxidase Mimetics as Novel Treatment Strategy," *Human Molecular Genetics* 11(24):3055-3063.

Jauslin, M.L. et al. (2003, e-pub. Aug. 15, 2003). "Mitochondria-Targeted Antioxidants Protect Friedreich Ataxia Fibroblasts from Endogenous Oxidative Stress More Effectively Than Untargeted Antioxidants" *The FASEB Journal* 17(13):1972-1974.

Kaufmann, P. et al. (Apr. 27, 2004). "Cerebral Lactic Acidosis Correlates with Neurological Impairment in MELAS," *Neurology* 62(8):1297-1302.

Kim, J.Y. et al. (May 2004). "Urinary 8-Hydroxy-2'-Deoxyguanosine as a Biomarker of Oxidative DNA Damage in Workers Exposed to Fine Particulates," *Environmental Health Perspectives* 112(6):666-671.

Lamperti, C. et al. (2003). "Cerebellar Ataxia and Coenzyme Q10 Deficiency," *Neurology* 60:1206:1208.

Lee, P.I. (1992). "Diffusion-Controlled Matrix Systems," Chapter 3 in *Treatise on Controlled Dug Delivery*, Kydonieus, A. ed., Marcel Dekker, Inc., New York, NY, pp. 155-197.

Lynch, D.R. et al. (May 2002, e-pub. Feb. 25, 2002). "Near Infrared Muscle Spectroscopy in Patients with Friedreich's Ataxia," *Muscle Nerve* 25(5):664-673.

Matthews, P.M. et al. (Apr. 1991). "In Vivo Magnetic Resonance Spectroscopy of Brain and Muscle in a Type of Mitochondrial Encephalomyopathy (MERRF)," *Ann. Neurol.* 29(4):435-438.

Munnich, A. et al. (1992). "Clinical Aspects of Mitochondrial Disorders," *Journal of Inherited Metabolic Disease* 15(4):448-455.

Musumeci, O. et al. (2001). "Familial Cerebellar Ataxia with Muscle Coenzyme Q10 Deficiency," *Neurology* 56:849-855.

Non-Final Office Action mailed May 31, 2013, for U.S. Appl. No. 12/997,869, filed Dec. 13, 2010, 24 pages.

Notice of Allowance mailed Dec. 18, 2013, for U.S. Appl. No. 12/997,869, filed Dec. 13, 2010, six pages.

Notice of Allowance mailed Mar. 6, 2014, for U.S. Appl. No. 12/997,869, filed Dec. 13, 2010, two pages.

Pfeffer et al. (2012). *Cochrane Database of Systemic Reviews*, Issue 4:1-42.

Pilger, A. et al. (2001). "Longitudinal Study of Urinary 8-Hydroxy-2'-Deoxyguanosine Excretion in Healthy Adults," *Free Radio. Res.* 35(3):273-280.

Piña, I.L. et al. (2003). "Exercise and Heart Failure: A Statement from the American Heart Association Committee on Exercise, Rehabilitation, and Prevention," *Circulation* 107:1210-1225.

Pulsinelli, W.A. (2000). "Ischemic Cerebrovascular Disease," Chapter 470 and "Hemorrhagic Cerebrovascular Disease," Chapter 471 in *Cecil Textbook of Medicine*, 21$^{st}$ Edition, Goldman, L. ed. et al., W.B. Saunders Company: Philadelphia, PA, pp. 2099-2115.

Rolfe, P. (2000). "In Vivo Near-Infrared Spectroscopy," *Annual Review of Biomedical Engineering* 2:715-754.

Strangman, G. et al. (2002). "Non-Invasive Neuroimaging Using Near-Infrared Light," *Biol. Psychiatry* 52:679-693.

Taivassalo, T. et al. (Jan. 2002, e-pub. Nov. 15, 2001). "Venous Oxygen Levels During Aerobic Forearm Exercise: An Index of Impaired Oxidative Metabolism in Mitochondrial Myopathy," *Ann. Neurol.* 51(1):38-44.

Taivassalo, T. et al. (2003). "The Spectrum of Exercise Tolerance in Mitochondrial Myopathies: A Study of 40 Patients," *Brain* 126:413-423.

Ueda, K. et al. (Feb. 1997). "Evaluation of Changes in Hepatic Energy Metabolism During Exercise by Ketone Body Ratio in Humans," *J. Cardiol.* 29(2):95-102. (Translation of Abstract Only).

(56) References Cited

OTHER PUBLICATIONS

Valko, M. et al. (2004). "Role of Oxygen Radicals in DNA Damage and Cancer Incidence," *Molecular and Cellular Biochemistry* 266:37-56.

Van Beekvelt, M.C.P. et al. (Oct. 1999). "Quantitative Near-Infrared Spectroscopy Discriminates Between Mitochondrial Myopathies and Normal Muscle," *Annals of Neurology* 46(4):667-670.

Wyman et al. (2010) *Cleveland Clinic Journal of Medicine*, vol. 77(7):435-442.

International Preliminary Report on Patentability mailed on Jan. 5, 2011, for PCT Patent Application No. PCT/US2009/048308, filed on Jun. 23, 2009, one page.

International Search Report mailed on Sep. 16, 2009, for PCT Patent Application No. PCT/US09/48308, filed on Jun. 23, 2009, two pages.

Written Opinion mailed on Sep. 16, 2009, for PCT Patent Application No. PCT/US09/48308, filed on Jun. 23, 2009, five pages.

\* cited by examiner

2-HETEROCYCLYLAMINOALKYL-(P-QUINONE) DERIVATIVES FOR TREATMENT OF OXIDATIVE STRESS DISEASES

CROSS-REFERENCE TO RELATED APPLICATIONS

This application is a divisional of U.S. patent application Ser. No. 12/997,869 submitted under 35 U.S.C. §371 as a U.S. National Stage Application of International Application No. PCT/US2009/048308 and having an International Filing Date of Jun. 23, 2009, now issued as U.S. Pat. No. 8,716,486, which claims priority benefit of U.S. Provisional Patent Application No. 61/133,169, filed Jun. 25, 2008. The entire contents of those applications are hereby incorporated by reference in their entirety.

TECHNICAL FIELD

The application discloses compositions and methods useful for treatment, prevention, or suppression of diseases, developmental delays and symptoms related to oxidative stress affecting normal electron flow in the cells. Examples of such diseases are mitochondrial disorders, impaired energy processing disorders, neurodegenerative diseases and diseases of aging.

BACKGROUND

Oxidative stress is caused by disturbances to the normal redox state within cells. An imbalance between routine production and detoxification of reactive oxygen species such as peroxides and free radicals can result in oxidative damage to the cellular structure and machinery. The most important source of reactive oxygen species under normal conditions in aerobic organisms is probably the leakage of activated oxygen from mitochondria during normal oxidative respiration. Impairments associated with this process are suspected to contribute to mitochondrial disease, neurodegenerative disease, and diseases of aging.

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Krebs cycle), which generates reduced nicotinamide adenine dinucleotide ($NADH+H^+$) from oxidized nicotinamide adenine dinucleotide ($NAD^+$), and oxidative phosphorylation, during which $NADH+H^+$ is oxidized back to $NAD^+$. (The citric acid cycle also reduces flavin adenine dinucleotide, or FAD, to $FADH_2$; $FADH_2$ also participates in oxidative phosphorylation.)

The electrons released by oxidation of $NADH+H^+$ are shuttled down a series of protein complexes (Complex I, Complex II, Complex III, and Complex IV) known as the mitochondrial respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

When cells in an organism are temporarily deprived of oxygen, anaerobic respiration is utilized until oxygen again becomes available or the cell dies. The pyruvate generated during glycolysis is converted to lactate during anaerobic respiration. The buildup of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Oxygen poisoning or toxicity is caused by high concentrations of oxygen that may be damaging to the body and increase the formation of free-radicals and other structures such as nitric oxide, peroxynitrite, and trioxidane. Normally, the body has many defense systems against such damage but at higher concentrations of free oxygen, these systems are eventually overwhelmed with time, and the rate of damage to cell membranes exceeds the capacity of systems which control or repair it. Cell damage and cell death then results.

Qualitative and/or quantitative disruptions in the transport of oxygen to tissues result in energy disruption in the function of red cells and contribute to various diseases such as haemoglobinopathies. Haemoglobinopathy is a kind of genetic defect that results in abnormal structure of one of the globin chains of the hemoglobin molecule. Common haemoglobinopathies include thalassemia and sickle-cell disease. Thalassemia is an inherited autosomal recessive blood disease. In thalassemia, the genetic defect results in reduced rate of synthesis of one of the globin chains that make up hemoglobin. While thalassemia is a quantitative problem of too few globins synthesized, sickle-cell disease is a qualitative problem of synthesis of an incorrectly functioning globin. Sickle-cell disease is a blood disorder characterized by red blood cells that assume an abnormal, rigid, sickle shape. Sickling decreases the cells' flexibility and results in their restricted movement through blood vessels, depriving downstream tissues of oxygen.

Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. Some examples of mitochondrial diseases are Friedreich's ataxia (FRDA), Leber's Hereditary Optic Neuropathy (LHON), mitochondrial myopathy, encephalopathy, lactacidosis, and stroke (MELAS), Myoclonus Epilepsy Associated with Ragged-Red Fibers (MERRF) syndrome, Leigh's disease, and respiratory chain disorders. Most mitochondrial diseases involve children who manifest the signs and symptoms of accelerated aging, including neurodegenerative diseases, stroke, blindness, hearing impairment, vision impairment, diabetes, and heart failure.

Friedreich's ataxia is an autosomal recessive neurodegenerative and cardiodegenerative disorder caused by decreased levels of the protein Frataxin. The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

Leber's Hereditary Optic Neuropathy (LHON) is a disease characterized by blindness which occurs on average between 27 and 34 years of age. Other symptoms may also occur, such as cardiac abnormalities and neurological complications.

Mitochondrial myopathy, encephalopathy, lactacidosis, and stroke (MELAS) can manifest itself in infants, children, or young adults. Strokes, accompanied by vomiting and seizures, are one of the most serious symptoms; it is postulated that the metabolic impairment of mitochondria in certain areas of the brain is responsible for cell death and neurological lesions, rather than the impairment of blood flow as occurs in ischemic stroke.

Myoclonus Epilepsy Associated with Ragged-Red Fibers (MERRF) syndrome is one of a group of rare muscular disorders that are called mitochondrial encephalomyopathies. Mitochondrial encephalomyopathies are disorders in which a defect in the genetic material arises from a part of the cell structure that releases energy (mitochondria). This can cause a dysfunction of the brain and muscles (encephalomyopathies). The mitochondrial defect as well as "ragged-red fibers" (an abnormality of tissue when viewed under a microscope) are always present. The most characteristic symptom of MERRF syndrome is myoclonic seizures that are usually sudden, brief, jerking, spasms that can affect the limbs or the entire body, difficulty speaking (dysarthria), optic atrophy, short stature, hearing loss, dementia, and involuntary jerking of the eyes (nystagmus) may also occur.

Leigh's disease is a rare inherited neurometabolic disorder characterized by degeneration of the central nervous system where the symptoms usually begin between the ages of 3 months to 2 years and progress rapidly. In most children, the first signs may be poor sucking ability and loss of head control and motor skills. These symptoms may be accompanied by loss of appetite, vomiting, irritability, continuous crying, and seizures. As the disorder progresses, symptoms may also include generalized weakness, lack of muscle tone, and episodes of lactic acidosis, which can lead to impairment of respiratory and kidney function. Heart problems may also occur.

Co-Enzyme Q10 Deficiency is a respiratory chain disorder, with syndromes such as myopathy with exercise intolerance and recurrent myoglobin in the urine manifested by ataxia, seizures or mental retardation and leading to renal failure (Di Mauro et al., (2005) *Neuromusc. Disord.,* 15:311-315), childhood-onset cerebellar ataxia and cerebellar atrophy (Masumeci et al., (2001) *Neurology* 56:849-855 and Lamperti et al., (2003) 60:1206:1208); and infantile encephalomyopathy associated with nephrosis. Biochemical measurement of muscle homogenates of patients with CoQ10 deficiency showed severely decreased activities of respiratory chain complexes I and II+III, while complex IV (COX) was moderately decreased (Gempel et al., (2007) *Brain*, 130(8):2037-2044).

Complex I Deficiency or NADH dehydrogenase NADH-CoQ reductase deficiency is a respiratory chain disorder, with symptoms classified by three major forms: (1) fatal infantile multisystem disorder, characterized by developmental delay, muscle weakness, heart disease, congenital lactic acidosis, and respiratory failure; (2) myopathy beginning in childhood or in adult life, manifesting as exercise intolerance or weakness; and (3) mitochondrial encephalomyopathy (including MELAS), which may begin in childhood or adult life and consists of variable combinations of symptoms and signs, including ophthalmoplegia, seizures, dementia, ataxia, hearing loss, pigmentary retinopathy, sensory neuropathy, and uncontrollable movements.

Complex II Deficiency or Succinate dehydrogenase deficiency is a respiratory chain disorder with symptoms including encephalomyopathy and various manifestations, including failure to thrive, developmental delay, hypotonia, lethargy, respiratory failure, ataxia, myoclonus and lactic acidosis.

Complex III Deficiency or Ubiquinone-cytochrome C oxidoreductase deficiency is a respiratory chain disorder with symptoms categorized in four major forms: (1) fatal infantile encephalomyopathy, congenital lactic acidosis, hypotonia, dystrophic posturing, seizures, and coma; (2) encephalomyopathies of later onset (childhood to adult life): various combinations of weakness, short stature, ataxia, dementia, hearing loss, sensory neuropathy, pigmentary retinopathy, and pyramidal signs; (3) myopathy, with exercise intolerance evolving into fixed weakness; and (4) infantile histiocytoid cardiomyopathy.

Complex IV Deficiency or Cytochrome C oxidase deficiency is a respiratory chain disorder with symptoms categorized in two major forms: (1) encephalomyopathy, where patients typically are normal for the first 6 to 12 months of life and then show developmental regression, ataxia, lactic acidosis, optic atrophy, ophthalmoplegia, nystagmus, dystonia, pyramidal signs, respiratory problems and frequent seizures; and (2) myopathy with two main variants: (a) Fatal infantile myopathy—may begin soon after birth and accompanied by hypotonia, weakness, lactic acidosis, ragged-red fibers, respiratory failure, and kidney problems: and (b) Benign infantile myopathy—may begin soon after birth and accompanied by hypotonia, weakness, lactic acidosis, ragged-red fibers, respiratory problems, but (if the child survives) followed by spontaneous improvement.

Complex V Deficiency or ATP synthase deficiency is a respiratory chain disorder including symptoms such as slow, progressive myopathy.

CPEO or Chronic Progressive External Ophthalmoplegia Syndrome is a respiratory chain disorder including symptoms such as visual myopathy, retinitis pigmentosa, or dysfunction of the central nervous system.

Kearns-Sayre Syndrome (KSS) is a mitochondrial disease characterized by a triad of features including: (1) typical onset in persons younger than age 20 years; (2) chronic, progressive, external ophthalmoplegia; and (3) pigmentary degeneration of the retina. In addition, KSS may include cardiac conduction defects, cerebellar ataxia, and raised cerebrospinal fluid (CSF) protein levels (e.g., >100 mg/dL). Additional features associated with KSS may include myopathy, dystonia, endocrine abnormalities (e.g., diabetes, growth retardation or short stature, and hypoparathyroidism), bilateral sensorineural deafness, dementia, cataracts, and proximal renal tubular acidosis.

In addition to congenital disorders involving inherited defective mitochondria, acquired mitochondrial dysfunction contributes to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitotoxic, neuronal injury, such as that associated with cerebral vascular accidents, seizures and ischemia.

The diseases above appear to be caused by defects in Complex I of the respiratory chain. Electron transfer from Complex I to the remainder of the respiratory chain is mediated by the compound coenzyme Q (also known as Ubiquinone). Oxidized coenzyme Q ($CoQ^{ox}$ or Ubiquinone) is reduced by Complex I to reduced coenzyme Q ($CoQ^{red}$ or Ubiquinol).

The reduced coenzyme Q then transfers its electrons to Complex III of the respiratory chain (skipping over complex II), where it is re-oxidized to $CoQ^{ox}$ (Ubiquinone). $CoQ^{ox}$ can then participate in further iterations of electron transfer.

Very few treatments are available for patients suffering from these mitochondrial diseases. Recently, the compound Idebenone has been proposed for treatment of Friedreich's ataxia. While the clinical effects of Idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Pat. No. 7,179,928); clinical results for MitoQ have not yet been reported. Administration of coenzyme Q10 (CoQ10) and vitamin supplements has shown only transient beneficial effects in individual cases of KSS. CoQ10 supplementation has also been used for the treatment of CoQ10 deficiency with mixed results.

Oxidative stress is suspected to be important in neurodegenerative diseases such as Motor Neuron Disease, Amyotrophic Lateral Sclerosis (ALS), Creutzfeldt-Jakob disease, Machado-Joseph disease, Spino-cerebellar ataxia, Multiple sclerosis (MS), Parkinson's disease, Alzheimer's disease, and Huntington's disease. Oxidative stress is thought to be linked to certain cardiovascular disease and also plays a role in the ischemic cascade due to oxygen reperfusion injury following hypoxia. This cascade includes both strokes and heart attacks.

Damage accumulation theory, also known as the free radical theory of aging, invokes random effects of free radicals produced during aerobic metabolism that cause damage to DNA, lipids and proteins and accumulate over time. The concept of free radicals playing a role in the aging process was first introduced by Himan D (1956), Aging—A theory based on free-radical and radiation chemistry *J. Gerontol.* 11, 298-300.

According to the free radical theory of aging, the process of aging begins with oxygen metabolism (Valko et al, (2004) Role of oxygen radicals in DNA damage and cancer incidence, *Mol. Cell. Biochem.*, 266, 37-56). Even under ideal conditions some electrons "leak" from the electron transport chain. These leaking electrons interact with oxygen to produce superoxide radicals, so that under physiological conditions, about 1-3% of the oxygen molecules in the mitochondria are converted into superoxide. The primary site of radical oxygen damage from superoxide radical is mitochondrial DNA (mtDNA) (Cadenas et al., (2000) Mitochondrial free radical generation, oxidative stress and aging, *Free Radic. Res*, 28, 601-609). The cell repairs much of the damage done to nuclear DNA (nDNA) but mtDNA cannot be fixed. Therefore, extensive mtDNA damage accumulates over time and shuts down mitochondria causing cells to die and the organism to age.

Some of the diseases associated with increasing age are cancer, diabetes mellitus, hypertension, atherosclerosis, ischemia/reperfusion injury, rheumatoid arthritis, neurodegenerative disorders such as dementia, Alzheimer's and Parkinson's. Diseases resulting from the process of aging as a physiological decline include decreases in muscle strength, cardiopulmonary function, vision and hearing as well as wrinkled skin and graying hair.

The ability to adjust biological production of energy has applications beyond the diseases described above. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. For example, if an individual is undergoing an extremely strenuous undertaking, it can be desirable to raise the level of ATP in that individual.

DISCLOSURE OF THE INVENTION

In one embodiment, the invention embraces a method of treating an oxidative stress disorder, including an oxidative stress disorder affecting normal electron flow in the cells, a disease caused by oxidative stress, a disease aggravated by oxidative stress, a primary oxidative stress disorder, a secondary oxidative stress disorder; or modulating one or more energy biomarkers, normalizing one or more energy biomarkers, or enhancing one or more energy biomarkers, comprising administering to a subject a therapeutically effective amount or effective amount of one or more compounds of formula I:

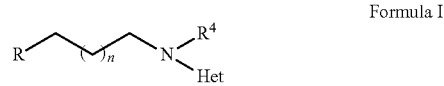

Formula I where R is selected from the group consisting of:

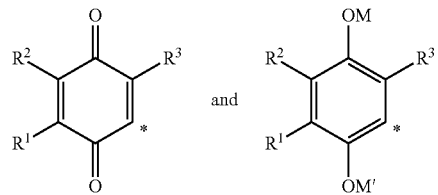

where the * indicates the point of attachment of R to the remainder of the molecule;

n is 0 or 1;

$R^1$ and $R^2$ are independently selected from hydrogen, $(C_1-C_6)$ alkyl, and $(C_1-C_6)$alkoxy;

$R^3$ is $(C_1-C_6)$alkyl or $(C_1-C_6)$alkoxy;

$R^4$ is hydrogen, $(C_1-C_6)$alkyl, hydroxy, or $(C_1-C_6)$alkoxy;

Het is optionally substituted heterocyclyl;

M and M' are independently selected from hydrogen, —C(O)—$R^{10}$, —C(O)($C_2-C_6$)-alkenyl, —C(O)($C_2-C_6$)-alkynyl, —C(O)-aryl, —C(O)-heterocyclyl, —C(O)O—$R^{10}$, —C(O)$NR^{10a}R^{10b}$, —$SO_2OR^{10}$, —$SO_2$—$C_1-C_6$-alkyl, —$SO_2$—($C_1-C_6$)-haloalkyl, —$SO_2$-aryl, —$SO_2$—$NR^{10a}R^{10b}$, and —P(O)($OR^{10a}$)($OR^{10b}$), and C-linked amino acid or di-peptide, and $R^{10}$, $R^{10a}$, and $R^{10b}$ are independently hydrogen or $(C_1-C_6)$-alkyl optionally substituted with OH, —$NH_2$, —NH($C_1-C_4$ alkyl), —N($C_1-C_4$ alkyl)$_2$, —C(O)OH, —C(O)O—($C_1-C_4$)-alkyl or halogen;

and all salts, prodrugs, metabolites, solvates, and hydrates thereof.

In one embodiment, the invention embraces compounds of formula I:

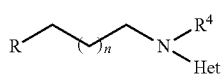

Formula I where R is selected from the group consisting of:

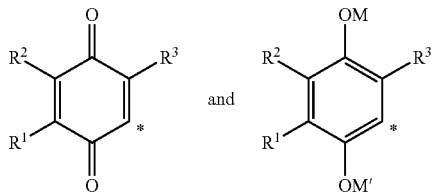

and where the * indicates the point of attachment of R to the remainder of the molecule;
n is 0 or 1;
$R^1$ and $R^2$ are independently selected from hydrogen, $(C_1-C_6)$ alkyl, and $(C_1-C_6)$alkoxy;
$R^3$ is $(C_1-C_6)$alkyl or $(C_1-C_6)$alkoxy;
$R^4$ is hydrogen, $(C_1-C_6)$alkyl, hydroxy, or $(C_1-C_6)$alkoxy;
Het is optionally substituted heterocyclyl;
M and M' are independently selected from hydrogen, —C(O)—$R^{10}$, —C(O)($C_2-C_6$)-alkenyl, —C(O)($C_2-C_6$)-alkynyl, —C(O)-aryl, —C(O)-heterocyclyl, —C(O)O—$R^{10}$, —C(O)N$R^{10a}R^{10b}$, $SO_2OR^{10}$, $SO_2$—$C_1-C_6$-alkyl, —$SO_2$—($C_1-C_6$)-haloalkyl, —$SO_2$-aryl, —$SO_2$—N$R^{10a}R^{10b}$, and —P(O)(O$R^{10a}$)(O$R^{10b}$), and C-linked amino acid or di-peptide, and
$R^{10}$, $R^{10a}$, and $R^{10b}$ are independently hydrogen or $(C_1-C_6)$-alkyl optionally substituted with —OH, —$NH_2$, —NH($C_1-C_4$ alkyl), —N($C_1-C_4$ alkyl)$_2$, —C(O)OH, —C(O)O—($C_1-C_4$)-alkyl or halogen;
with the proviso that the compound is not 2-(2-(9-(3,4-dihydroxy-5-(hydroxymethyl)tetrahydrofuran-2-yl)-9H-purin-6-ylamino)ethyl)-3,5,6-trimethylcyclohexa-2,5-diene-1,4-dione or 2-(2-(9-(3,4-dihydroxy-5-(hydroxymethyl)tetrahydrofuran-2-yl)-9H-purin-6-ylamino)ethyl)-3,5,6-trimethoxycyclohexa-2,5-diene-1,4-dione.
and all salts, prodrugs, metabolites, solvates, and hydrates thereof.

In some embodiments, the invention embraces compounds wherein $R^1$, $R^2$ and $R^3$ are independently $C_1$-$C_6$-alkyl. In other embodiments, $R^1$ and $R^2$ are independently $C_1$-$C_6$-alkoxy and $R^3$ is $C_1$-$C_6$-alkyl. In other embodiments, one of $R^1$ and $R^2$ is $C_1$-$C_6$-alkoxy and the other is hydrogen, and $R^3$ is independently $C_1$-$C_6$-alkyl. In other embodiments, one of $R^1$ and $R^2$ is $C_1$-$C_6$-alkoxy, the other is $C_1$-$C_6$-alkyl, and $R^3$ is independently $C_1$-$C_6$-alkyl. In some embodiments, the invention embraces compounds wherein $R^1$, $R^2$ and $R^3$ are methyl. In other embodiments, $R^1$, and $R^2$ are methoxy and $R^3$ is methyl. In other embodiments, one of $R^1$ and $R^2$ is methoxy, the other is hydrogen, and $R^3$ is methyl. In other embodiments, one of $R^1$ and $R^2$ is methoxy, the other is methyl, and $R^3$ is methyl.

In another embodiment, the invention embraces a method of treating or suppressing an oxidative stress disorder, including an oxidative stress disorder affecting normal electron flow in the cells, a disease caused by oxidative stress, a disease aggravated by oxidative stress, a primary oxidative stress disorder, a secondary oxidative stress disorder, where the disorder is selected from a mitochondrial disorder, an impaired energy processing disorder, a neurodegenerative disorder and a disease of aging; or modulating one or more energy biomarkers, normalizing one or more energy biomarkers, or enhancing one or more energy biomarkers, by administering a therapeutically effective amount or effective amount of one or more compounds of formula I as described above. In some embodiments the disorder is Friedreich's ataxia. In other embodiments, the disorder is MELAS. In other embodiments, the disorder is LHON. In other embodiments the disorder is MERFF. In another embodiment, the disorder is Leigh's disease.

In another embodiment, the invention embraces a method of treating or suppressing a mitochondrial disorder of the respiratory chain. In particular embodiments, the disorder is Coenzyme Q10 deficiency. In other particular embodiments, the disorder is a defect of Complex I or Complex II or Complex III or Complex IV or Complex V or a combination thereof.

In another embodiment, the invention embraces a method of treating disorders where qualitative and/or quantitative disruptions in the transport of oxygen to tissues result in energy disruption in the function of red cells. Some of these diseases include oxygen poisoning and haemoglobinopathies, such as sickle-cell disease and thalassemia.

In another embodiment, the invention embraces a method of treating or suppressing a neurodegenerative disorder. In particular embodiments, the neurodegenerative disorder is a disorder associated with aging. In other particular embodiments, the disorder is Huntington's, Parkinson's or Alzheimer's disease. In other particular embodiments, the disorder is related to a neurodegenerative disorder resulting in hearing or balance impairment. In other particular embodiments, the disorder is related to a neurodegenerative disorder resulting in vision impairment.

In another embodiment, the invention embraces compounds of formula Ia:

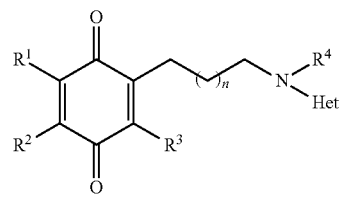

Formula Ia where:
n is 0 or 1;
$R^1$ and $R^2$ are independently selected from hydrogen, $(C_1-C_6)$ alkyl, and $(C_1-C_6)$alkoxy;
$R^3$ is $(C_1-C_6)$alkyl or $(C_1-C_6)$alkoxy;
$R^4$ is hydrogen, $(C_1-C_6)$alkyl, hydroxy, or $(C_1-C_6)$alkoxy;
Het is heterocyclyl optionally substituted with $(C_1-C_6)$alkyl, $(C_1-C_6)$haloalkyl, halogen, nitro, cyano, —C(O)($C_1-C_4$) alkyl, —C(O)($C_1-C_6$)cycloalkyl, —C(O)OH, —C(O)O ($C_1-C_4$)-alkyl or oxo;
and all salts, prodrugs, metabolites, solvates, and hydrates thereof.

In one embodiment, the invention embraces compounds of formula Ia, where n is 0; in another embodiment the invention embraces compounds of formula Ia, where n is 1.

In one embodiment, the invention embraces compounds of formula Ia, where $R^1$, $R^2$, and $R^3$ are independently $(C_1-C_4)$ alkyl; and all salts, prodrugs, metabolites, solvates, and hydrates thereof. In some embodiments, $R^1$, $R^2$, and $R^3$ are methyl.

In another embodiment, the invention embraces compounds of formula Ia, where $R^4$ is hydrogen, and all salts, prodrugs, metabolites, solvates, and hydrates thereof.

In another embodiment, the invention embraces compounds of formula Ia, where $R^4$ is ($C_1$-$C_4$)alkyl, such as methyl.

In another embodiment, the invention embraces compounds of formula Ia, where $R^1$, $R^2$, $R^3$ and R are independently ($C_1$-$C_4$)alkyl, and all salts, prodrugs, metabolites, solvates, and hydrates thereof. In some embodiments, $R^1$, $R^2$, $R^3$, and $R^4$ are methyl.

In another embodiment, the invention embraces compounds of formula Ia, where $R^1$, $R^2$, and $R^3$ are independently ($C_1$-$C_4$)alkyl and $R^4$ is hydrogen; and all salts, prodrugs, metabolites, solvates, and hydrates thereof. In some embodiments, $R^1$, $R^2$, and $R^3$ are methyl and $R^4$ is hydrogen, and all salts, prodrugs, metabolites, solvates, and hydrates thereof.

In another embodiment, the invention embraces compounds of formula Ia, where $R^1$, $R^2$, and $R^3$ are independently ($C_1$-$C_4$)alkoxy, and all salts, prodrugs, metabolites, solvates, and hydrates thereof. In some embodiments, $R^1$, $R^2$, and $R^3$ are methoxy.

In another embodiment, the invention embraces compounds of formula Ia, where $R^1$, $R^2$, $R^3$, and $R^4$ are independently ($C_1$-$C_4$)alkoxy, and all salts, prodrugs, metabolites, solvates, and hydrates thereof. In some embodiments, $R^1$, $R^2$, $R^3$, and $R^4$ are methoxy.

In another embodiment, the invention embraces compounds of formula Ia, where $R^1$ and $R^2$ are independently ($C_1$-$C_4$)alkoxy, and $R^3$ is ($C_1$-$C_4$)alkyl, and all salts, prodrugs, metabolites, solvates, and hydrates thereof. In some embodiments, $R^1$ and $R^2$ are methoxy and $R^3$ is methyl.

In another embodiment, the invention embraces compounds of formula Ia, where $R^1$ and $R^2$ are independently ($C_1$-$C_4$)alkoxy, $R^3$ is ($C_1$-$C_4$)alkyl, and $R^4$ is hydrogen and all salts, prodrugs, metabolites, solvates, and hydrates thereof. In some embodiments, $R^1$ and $R^2$ are methoxy, $R^3$ is methyl, and $R^4$ is hydrogen.

In some embodiments, the invention embraces compounds of formula Ia, where Het is an optionally substituted saturated or partially unsaturated heterocyclyl; and all salts, prodrugs, metabolites, solvates, and hydrates thereof. In some embodiments, the invention embraces compounds of formula Ia where Het is optionally substituted piperidine, morpholine, piperazine, thiazolidine, pyrazolidine, pyrazoline, imidazolidine, pyrrolidine, tetrahydropyran, tetrahydrofuran, quinuclidine, and all salts, prodrugs, metabolites, solvates, and hydrates thereof.

In some embodiments, the invention embraces compounds of formula Ia, where Het is an optionally substituted heteroaryl; and all salts, prodrugs, metabolites, solvates, and hydrates thereof.

In another embodiment, the invention embraces compounds of formula Ia, where Het is an optionally substituted nitrogen containing heteroaryl. In some embodiments Het is selected from optionally substituted pyridine, pyrrole, pyrazole, imidazole, pyrimidine, pyridazine, pyrazine, oxazole, thiazole, or tetrazole, and all salts, prodrugs, metabolites, solvates, and hydrates thereof. In other embodiments, Het is selected from optionally substituted indole, quinoline, isoindole, isoquinoline, indazole, benzimidazole, cinnoline, quinazoline, quinoxaline, phthalazine, benzotriazole, imidazo-pyridine, pyrazolo-pyrazine, pyrazolo-pyridazine, tetrahydropurine, pyrimido-pyrimidine, pyrazino-pyridazine, acridine, dibenzazepine, carbazole, phenanthridine, phenazine, benzoxazole, benzisoxazole, benzoxazine, phenoxazine, benzothiazole, benzoisothiazole, benzothiazine, and all salts, prodrugs, metabolites, solvates, and hydrates thereof. In some embodiments, Het is pyridine, pyrimidine, 4-trifluoromethyl-pyrimidin-2-yl, 4-trifluoromethyl-pyridin-2-yl, 5-trifluoromethyl-pyridin-2-yl; 6-trifluoromethyl-pyridin-2-yl, 3-trifluoromethyl-pyridin-2-yl, 5-fluoro-pyridin-2-yl, 4-fluoro-pyridin-2-yl and all salts, prodrugs, metabolites, solvates, and hydrates thereof.

In another embodiment, the invention embraces compounds of formula Ia, where Het is an optionally substituted oxygen or sulfur containing heteroaryl. In some embodiments, Het is selected from optionally substituted furan, pyran, thiophene, thiopyran, benzofuran, benzopyran, benzodioxole, xanthene, benzothiophene, benzothiopyran, and thioxanthene, and all salts, prodrugs, metabolites, solvates, and hydrates thereof.

In another embodiment, the invention embraces compounds of the formula Ib:

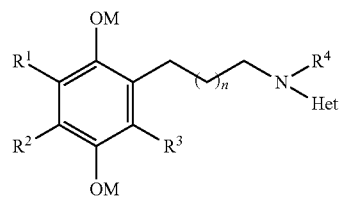

Formula Ib where:

n is 0 or 1;

$R^1$ and $R^2$ are independently selected from hydrogen, ($C_1$-$C_6$)alkyl, and ($C_1$-$C_6$)alkoxy;

$R^3$ is ($C_1$-$C_6$)alkyl or ($C_1$-$C_6$)alkoxy;

$R^4$ is hydrogen, ($C_1$-$C_6$)alkyl, hydroxy, or ($C_1$-$C_6$)alkoxy;

Het is heterocyclyl optionally substituted with ($C_1$-$C_6$)alkyl, ($C_1$-$C_6$)haloalkyl, halogen, nitro, cyano, —C(O)($C_1$-$C_4$)alkyl, —C(O)($C_1$-$C_6$)cycloalkyl, —C(O)OH, —C(O)O($C_1$-$C_4$)-alkyl or oxo;

M and M' are independently selected from hydrogen, —C(O)—$R^{10}$, —C(O)($C_2$-$C_6$)-alkenyl, —C(O)($C_2$-$C_6$)alkynyl, —C(O)aryl, —C(O)heterocyclyl, —C(O)O—$R^{10}$, —C(O)NR$^{10a}$R$^{10b}$, —SO$_2$OR$^{10}$, —SO$_2$—C$_1$-C$_6$-alkyl, —SO$_2$—($C_1$-$C_6$)-haloalkyl, —SO$_2$-aryl, —SO$_2$—NR$^{10a}$R$^{10b}$, and —P(O)(OR$^{10a}$)(OR$^{10b}$), and C-linked amino acid or di-peptide, and $R^{10}$, $R^{10a}$, and $R^{10b}$ are independently hydrogen or ($C_1$-$C_6$)-alkyl optionally substituted with OH, —NH$_2$, —NH($C_1$-$C_4$ alkyl), —N($C_1$-$C_4$ alkyl)$_2$, —C(O)OH, —C(O)O—($C_1$-$C_4$)-alkyl or halogen;

and all salts, prodrugs, metabolites, solvates, and hydrates thereof.

In one embodiment, the invention embraces compounds of formula Ib, where n is 0; in another embodiment the invention embraces compounds of formula Ib, where n is 1.

In one embodiment, the invention embraces compounds of formula Ib, where $R^1$, $R^2$, and $R^3$ are independently $C_1$-$C_4$-alkyl; and all salts, prodrugs, metabolites, solvates, and hydrates thereof. In some embodiments, $R^1$, $R^2$, and $R^3$ are methyl.

In another embodiment, the invention embraces compounds of formula Ib, where $R^4$ is hydrogen, and all salts, prodrugs, metabolites, solvates, and hydrates thereof.

In another embodiment, the invention embraces compounds of formula Ib, where $R^4$ is $C_1$-$C_4$-alkyl, such as methyl.

In another embodiment, the invention embraces compounds of formula Ib, where $R^1$, $R^2$, $R^3$, and $R^4$ are independently $C_1$-$C_4$-alkyl, and all salts, prodrugs, metabolites, solvates, and hydrates thereof. In some embodiments, $R^1$, $R^2$, $R^3$, and $R^4$ are methyl.

In another embodiment, the invention embraces compounds of formula Ib, where $R^1$, $R^2$, and $R^3$ are independently $C_1$-$C_4$-alkyl and $R^4$ is hydrogen; and all salts, prodrugs, metabolites, solvates, and hydrates thereof. In some embodiments, $R^1$, $R^2$, and $R^3$ are methyl and $R^4$ is hydrogen, and all salts, prodrugs, metabolites, solvates, and hydrates thereof.

In another embodiment, the invention embraces compounds of formula Ib, where $R^1$, $R^2$, and $R^3$ are independently $C_1$-$C_4$-alkoxy, and all salts, prodrugs, metabolites, solvates, and hydrates thereof. In some embodiments, $R^1$, $R^2$, and $R^3$ are methoxy.

In another embodiment, the invention embraces compounds of formula Ib, where $R^1$, $R^2$, $R^3$, and $R^4$ are independently $C_1$-$C_4$-alkoxy, and all salts, prodrugs, metabolites, solvates, and hydrates thereof. In some embodiments, $R^1$, $R^2$, $R^3$, and $R^4$ are methoxy.

In another embodiment, the invention embraces compounds of formula Ib, where $R^1$ and $R^2$ are independently $C_1$-$C_4$-alkoxy, and $R^3$ is $C_1$-$C_4$-alkyl, and all salts, prodrugs, metabolites, solvates, and hydrates thereof. In some embodiments, $R^1$ and $R^2$ are methoxy and $R^3$ is methyl.

In another embodiment, the invention embraces compounds of formula Ib, where $R^1$ and $R^2$ are independently $C_1$-$C_4$-alkoxy, $R^3$ is $C_1$-$C_4$-alkyl, and $R^4$ is hydrogen and all salts, prodrugs, metabolites, solvates, and hydrates thereof. In some embodiments, $R^1$ and $R^2$ are methoxy, $R^3$ is methyl, and $R^4$ is hydrogen.

In some embodiments, the invention embraces compounds of formula Ib, where Het is an optionally substituted saturated or partially unsaturated heterocyclyl; and all salts, prodrugs, metabolites, solvates, and hydrates thereof. In some embodiments, the invention embraces compounds of formula Ib where Het is optionally substituted piperidine, morpholine, piperazine, thiazolidine, pyrazolidine, pyrazoline, imidazolidine, pyrrolidine, tetrahydropyran, tetrahydrofuran, quinuclidine, and all salts, prodrugs, metabolites, solvates, and hydrates thereof.

In some embodiments, the invention embraces compounds of formula Ib, where Het is an optionally substituted heteroaryl; and all salts, prodrugs, metabolites, solvates, and hydrates thereof.

In another embodiment, the invention embraces compounds of formula Ib, where Het is an optionally substituted nitrogen containing heteroaryl. In some embodiments Het is selected from optionally substituted pyridine, pyrrole, pyrazole, imidazole, pyrimidine, pyridazine, pyrazine, oxazole, thiazole, or tetrazole, and all salts, prodrugs, metabolites, solvates, and hydrates thereof. In other embodiments, Het is selected from optionally substituted indole, quinoline, isoindole, isoquinoline, indazole, benzimidazole, cinnoline, quinazoline, quinoxaline, phthalazine, benzotriazole, imidazo-pyridine, pyrazolo-pyrazine, pyrazolo-pyridazine, tetrahydropurine, pyrimido-pyrimidine, pyrazino-pyridazine, acridine, dibenzazepine, carbazole, phenanthridine, phenazine, benzoxazole, benzisoxazole, benzoxazine, phenoxazine, benzothiazole, benzoisothiazole, benzothiazine, and all salts, prodrugs, metabolites, solvates, and hydrates thereof. In some embodiments, Het is pyridine, pyrimidine, 4-trifluoromethyl-pyrimidin-2-yl, 4-trifluoromethyl-pyridin-2-yl, 5-trifluoromethyl-pyridin-2-yl; 6-trifluoromethyl-pyridin-2-yl, 3-trifluoromethyl-pyridin-2-yl, 4-fluoro-pyridin-2-yl, and all salts, prodrugs, metabolites, solvates, and hydrates thereof.

In another embodiment, the invention embraces compounds of formula Ib, where Het is an optionally substituted oxygen or sulfur containing heteroaryl. In some embodiments, Het is selected from optionally substituted furan, pyran, thiophene, thiopyran, benzofuran, benzopyran, benzodioxole, xanthene, benzothiophene, benzothiopyran, and thioxanthene, and all salts, prodrugs, metabolites, solvates, and hydrates thereof.

In another embodiment, the invention embraces compounds of formula Ib, where M and M' are independently selected from hydrogen, —C(O)—H or —C(O)—$C_1$-$C_6$-alkyl, for example hydrogen or acetyl, and all salts, prodrugs, metabolites, solvates, and hydrates thereof.

In another embodiment, the invention embraces compounds of formula Ib, where $R^1$, $R^2$, and $R^3$ are methyl and M and M' are independently hydrogen or C(O)—$R^{10}$, and salts, prodrugs, metabolites, solvates, and hydrates thereof. In another embodiment, the invention embraces compounds of formula Ib, where $R^1$, $R^2$, and $R^3$ are methyl and M and M' are independently hydrogen or acetyl, and salts, prodrugs, metabolites, solvates, and hydrates thereof.

In another embodiment, the invention embraces compounds of formula I, selected from:

2,3,5-trimethyl-6-(2-(pyrimidin-2-ylamino)ethyl)cyclohexa-2,5-diene-1,4-dione;

2,3,5-trimethyl-6-(2-(pyridin-2-ylamino)ethyl)cyclohexa-2,5-diene-1,4-dione;

2,3,5-trimethyl-6-(2-(4-(trifluoromethyl)pyrimidin-2-ylamino)ethyl)cyclohexa-2,5-diene-1,4-dione;

2,3,5-trimethyl-6-(2-(4-(trifluoromethyl)pyridin-2-ylamino)ethyl)cyclohexa-2,5-diene-1,4-dione;

2,3,5-trimethyl-6-(2-(5-(trifluoromethyl)pyridin-2-ylamino)ethyl)cyclohexa-2,5-diene-1,4-dione;

2,3,5-trimethyl-6-(2-(6-(trifluoromethyl)pyridin-2-ylamino)ethyl)cyclohexa-2,5-diene-1,4-dione;

2,3,5-trimethyl-6-(2-(3-(trifluoromethyl)pyridin-2-ylamino)ethyl)cyclohexa-2,5-diene-1,4-dione;

2-(2-(5-fluoropyrimidin-2-ylamino)ethyl)-3,5,6-trimethylcyclohexa-2,5-diene-1,4-dione;

2-(2-(4-fluoropyrimidin-2-ylamino)ethyl)-3,5,6-trimethylcyclohexa-2,5-diene-1,4-dione;

2,3,5-trimethyl-6-(2-(pyrazin-2-ylamino)ethyl)cyclohexa-2,5-diene-1,4-dione;

2-(2-(3-chloropyrazin-2-ylamino)ethyl)-3,5,6-trimethylcyclohexa-2,5-diene-1,4-dione;

2-(2-(6-chloropyrazin-2-ylamino)ethyl)-3,5,6-trimethylcyclohexa-2,5-diene-1,4-dione;

2-(2-(imidazo[1,2-a]pyridin-5-ylamino)ethyl)-3,5,6-trimethylcyclohexa-2,5-diene-1,4-dione;

2-(2-(1H-benzo[d]imidazol-2-ylamino)ethyl)-3,5,6-trimethylcyclohexa-2,5-diene-1,4-dione;

2-(2-(1H-indol-2-ylamino)ethyl)-3,5,6-trimethylcyclohexa-2,5-diene-1,4-dione;

2,3,5-trimethyl-6-(2-(quinolin-2-ylamino)ethyl)cyclohexa-2,5-diene-1,4-dione;

2-(2-(1H-imidazol-2-ylamino)ethyl)-3,5,6-trimethylcyclohexa-2,5-diene-1,4-dione;

2-(2-(1H-pyrrol-2-ylamino)ethyl)-3,5,6-trimethylcyclohexa-2,5-diene-1,4-dione;

2-(2-(1H-pyrazol-5-ylamino)ethyl)-3,5,6-trimethylcyclohexa-2,5-diene-1,4-dione;

2-(2-(1H-imidazol-5-ylamino)ethyl)-3,5,6-trimethylcyclohexa-2,5-diene-1,4-dione;

2,3,5-trimethyl-6-(2-(1-methyl-1H-imidazol-5-ylamino)
ethyl)cyclohexa-2,5-diene-1,4-dione;

2,3,5-trimethyl-6-(2-(oxazol-5-ylamino)ethyl)cyclohexa-2,
5-diene-1,4-dione;

2,3,5-trimethyl-6-(2-(oxazol-4-ylamino)ethyl)cyclohexa-2,
5-diene-1,4-dione;

2,3,5-trimethyl-6-(2-(thiazol-4-ylamino)ethyl)cyclohexa-2,
5-diene-1,4-dione;

2-(2-(furan-3-ylamino)ethyl)-3,5,6-trimethylcyclohexa-2,5-
diene-1,4-dione;

2,3,5-trimethyl-6-(2-(methyl(pyridin-2-yl)amino)ethyl)cy-
clohexa-2,5-diene-1,4-dione;

2,3,5-trimethyl-6-(3-(pyridin-2-ylamino)propyl)cyclohexa-
2,5-diene-1,4-dione;

2,3,5-trimethyl-6-(3-(pyrimidin-2-ylamino)propyl)cyclo-
hexa-2,5-diene-1,4-dione;

2,3,5-trimethyl-6-(3-(5-(trifluoromethyl)pyridin-2-ylamino)
propyl)cyclohexa-2,5-diene-1,4-dione;

2,3,5-trimethyl-6-(2-(tetrahydrofuran-3-ylamino)ethyl)cy-
clohexa-2,5-diene-1,4-dione; and 2,3,5-trimethyl-6-(2-(piperidin-2-ylamino)ethyl)cyclohexa-
2,5-diene-1,4-dione;

and all salts, prodrugs, metabolites, solvates, and hydrates thereof

In one embodiment, including any of the foregoing embodiments, the invention embraces a method of treating or suppressing an oxidative stress disorder, including an oxidative stress disorder affecting normal electron flow in the cells, a disease caused by oxidative stress, a disease aggravated by oxidative stress, a primary oxidative stress disorder, or a secondary oxidative stress disorder, selected from a mitochondrial disorder, an impaired energy processing disorder, a neurodegenerative disorder and a disease of aging; or modulating one or more energy biomarkers, normalizing one or more energy biomarkers, or enhancing one or more energy biomarkers, by administering a therapeutically effective amount or effective amount of one or more compounds of Formula I, Ia, or Ib, or any salt, prodrug, metabolite, solvate, or hydrate thereof.

In another embodiment, the invention embraces a method of treating or suppressing an oxidative stress disorder, including an oxidative stress disorder affecting normal electron flow in the cells, a disease caused by oxidative stress, a disease aggravated by oxidative stress, a primary oxidative stress disorder, a secondary oxidative stress disorder, selected from a mitochondrial disorder, an impaired energy processing disorder, a neurodegenerative disorder and a disease of aging; or modulating one or more energy biomarkers, normalizing one or more energy biomarkers, or enhancing one or more energy biomarkers, by administering a therapeutically effective amount or effective amount of one or more compounds of formula I, or any salt, prodrug, metabolite, solvate, or hydrate thereof.

In another embodiment, the invention embraces a method of treating or suppressing an oxidative stress disorder, including an oxidative stress disorder affecting normal electron flow in the cells, a disease caused by oxidative stress, a disease aggravated by oxidative stress, a primary oxidative stress disorder, a secondary oxidative stress disorder, selected from a mitochondrial disorder, an impaired energy processing disorder, a neurodegenerative disorder and a disease of aging; or modulating one or more energy biomarkers, normalizing one or more energy biomarkers, or enhancing one or more energy biomarkers, by administering a therapeutically effective amount or effective amount of one or more compounds of formula Ia, where $R^1$, $R^2$, and $R^3$ are independently $C_1$-$C_4$ alkyl; or any salt, prodrug, metabolite, solvate, or hydrate thereof.

In another embodiment, the invention embraces a method of treating or suppressing an oxidative stress disorder, including an oxidative stress disorder affecting normal electron flow in the cells, a disease caused by oxidative stress, a disease aggravated by oxidative stress, a primary oxidative stress disorder, a secondary oxidative stress disorder, selected from a mitochondrial disorder, an impaired energy processing disorder, a neurodegenerative disorder and a disease of aging; or modulating one or more energy biomarkers, normalizing one or more energy biomarkers, or enhancing one or more energy biomarkers, by administering a therapeutically effective amount or effective amount of one or more compounds of formula Ib, where $R^1$, $R^2$, and $R^3$ are independently selected from —$C_1$-$C_4$ alkyl and $R^4$ is hydrogen; or any salt, prodrug, metabolite, solvate, or hydrate thereof.

In other embodiments, including any of the foregoing embodiments, the disorder caused by oxidative stress or aggravated by oxidative stress is a mitochondrial disorder selected from the group consisting of mitochondrial diseases; Myoclonic Epilepsy with Ragged Red Fibers (MERRF); Mitochondrial Myopathy, Encephalopathy, Lactacidosis, and Stroke (MELAS); Leber's Hereditary Optic Neuropathy (LHON); chronic progressive external ophthalmoplegia (CPEO); Leigh Disease; Kearns-Sayre Syndrome (KSS); Friedreich's Ataxia (FRDA); Co-Enzyme Q10 (CoQ10) Deficiency; Complex I Deficiency; Complex II Deficiency; Complex III Deficiency; Complex IV Deficiency; Complex V Deficiency; other myopathies; cardiomyopathy; encephalomyopathy; renal tubular acidosis; neurodegenerative diseases; Parkinson's disease; Alzheimer's disease; amyotrophic lateral sclerosis (ALS); motor neuron diseases; hearing and balance impairments; vision impairments; other neurological disorders; epilepsy; genetic diseases; Huntington's Disease; mood disorders; schizophrenia; bipolar disorder; age-associated diseases; cerebral vascular diseases; macular degeneration; diabetes; and cancer.

In another embodiment, including any of the foregoing embodiments, the mitochondrial disorder is a mitochondrial respiratory chain disorder. In a particular embodiment, the mitochondrial respiratory chain disorder is a respiratory chain protein disorder. In another particular embodiment, the disorder is CoQ10 deficiency.

In another embodiment, including any of the foregoing embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, and Stroke (MELAS); Leber's Hereditary Optic Neuropathy (LHON); chronic progressive external ophthalmoplegia (CPEO); Leigh Disease; Kearns-Sayre Syndrome (KSS); and Friedreich's Ataxia (FRDA).

In another embodiment of the invention, including any of the foregoing embodiments, the mitochondrial disorder is Friedreich's Ataxia (FA). In another embodiment of the invention, including any of the foregoing embodiments, the mitochondrial disorder is Leber's Hereditary Optic Neuropathy (LHON). In another embodiment of the invention, including any of the foregoing embodiments, the mitochondrial disorder is mitochondrial myopathy, encephalopathy, lactacidosis, and stroke (MELAS). In another embodiment of the invention, including any of the foregoing embodiments, the mitochondrial disorder is Leigh disease. In another embodiment of the invention, including any of the foregoing embodiments, the mitochondrial disorder is Kearns-Sayre Syndrome (KSS). In another embodiment of the invention, including any of the foregoing embodiments, the mitochondrial disorder is Myoclonic Epilepsy with Ragged Red Fibers (MERRF). In another embodiment of the invention, including any of the foregoing embodiments, the disorder is CoQ10 Deficiency. In another embodiment of the invention, including any of the foregoing embodiments, the disorder is Parkinson's disease. In another embodiment of the invention, including any of the foregoing embodiments, the disorder is Huntington's disease. In another embodiment of the invention, including any of the foregoing embodiments, the disorder is amyotrophic lateral sclerosis (ALS). In yet another embodiment of the invention, including any of the foregoing embodiments, the disorders are cerebral vascular accidents, such as stroke. In another embodiment of the invention, including any of the foregoing embodiments, the disorder is hearing or balance impairment. In another embodiment of the invention, including any of the foregoing embodiments, the disorder is vision impairment.

In another embodiment of the invention, including any of the foregoing embodiments, the compounds described herein are administered to subjects affected with an impaired energy processing disorder due to deprivation, poisoning or toxicity of oxygen.

In another embodiment of the invention, including any of the foregoing embodiments, the compounds described herein are administered to subjects affected with diseases where qualitative and/or quantitative disruptions in the transport of oxygen to tissues result in energy disruption in the function of red cells. In another embodiment of the invention, including any of the foregoing embodiments, the diseases include haemoglobinopathies, such as sickle-cell disease and thalassemia.

In another embodiment of the invention, including any of the foregoing embodiments, the compounds described herein are administered to subjects suffering from a mitochondrial disorder to modulate one or more of various energy biomarkers, including, but not limited to, lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+H$^+$) or NADPH (NADPH+H$^+$) levels; NAD or NADP levels; ATP levels; reduced coenzyme Q (CoQ$^{red}$) levels; oxidized coenzyme Q (Car) levels; total coenzyme Q (CoQ$^{tot}$) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), respiratory quotient (VCO2/VO2), and to modulate exercise intolerance (or conversely, modulate exercise tolerance) and to modulate anaerobic threshold. Energy biomarkers can be measured in whole blood, plasma, cerebrospinal fluid, cerebroventricular fluid, arterial blood, venous blood, or any other body fluid, body gas, or other biological sample useful for such measurement. In one embodiment, the levels are modulated to a value within about 2 standard deviations of the value in a healthy subject. In another embodiment, the levels are modulated to a value within about 1 standard deviation of the value in a healthy subject. In another embodiment, the levels in a subject are changed by at least about 10% above or below the level in the subject prior to modulation. In another embodiment, the levels are changed by at least about 20% above or below the level in the subject prior to modulation. In another embodiment, the levels are changed by at least about 30% above or below the level in the subject prior to modulation. In another embodiment, the levels are changed by at least about 40% above or below the level in the subject prior to modulation. In another embodiment, the levels are changed by at least about 50% above or below the level in the subject prior to modulation. In another embodiment, the levels are changed by at least about 75% above or below the level in the subject prior to modulation. In another embodiment, the levels are changed by at least about 100% above or at least about 90% below the level in the subject prior to modulation.

In another embodiment, including any of the foregoing embodiments, the subject or subjects in which a method of treating or suppressing an oxidative stress disorder, modulating one or more energy biomarkers, normalizing one or more energy biomarkers, or enhancing one or more energy biomarkers is performed is/are selected from the group consisting of subjects undergoing strenuous or prolonged physical activity; subjects with chronic energy problems; subjects with chronic respiratory problems; pregnant females; pregnant females in labor; neonates; premature neonates; subjects exposed to extreme environments; subjects exposed to hot environments; subjects exposed to cold environments; subjects exposed to environments with lower-than-average oxygen content; subjects exposed to environments with higher-than-average carbon dioxide content; subjects exposed to environments with higher-than-average levels of air pollution; airline travelers; flight attendants; subjects at elevated altitudes; subjects living in cities with lower-than-average air quality; subjects working in enclosed environments where air quality is degraded; subjects with lung diseases; subjects with lower-than-average lung capacity; tubercular patients; lung cancer patients; emphysema patients; cystic fibrosis patients; subjects recovering from surgery; subjects recovering from illness; elderly subjects; elderly subjects experiencing decreased energy; subjects suffering from chronic fatigue; subjects suffering from chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

In another embodiment, the invention embraces one or more compounds of formula I, Ia, and/or Ib, in combination with a pharmaceutically acceptable excipient, carrier, or vehicle.

In another embodiment, the invention embraces the use of one or more compounds of formula I, Ia, and/or Ib, in the therapy of mitochondrial disease. In another embodiment, the invention embraces the use of one or more compounds of formula I, Ia, and/or Ib in the manufacture of a medicament for use in therapy of mitochondrial disease.

For all of the compounds and methods described above, the quinone form can also be used in its reduced (hydroquinone) form when desired. Likewise, the hydroquinone form can also be used in its oxidized (quinone) form when desired.

MODES FOR CARRYING OUT THE INVENTION

The invention embraces compounds useful in treating or suppressing diseases, developmental delays and symptoms related to oxidative stress such as mitochondrial disorders, impaired energy processing disorders, neurodegenerative diseases and diseases of aging, and methods of using such compounds for modulation of energy biomarkers. The redox active therapeutics for treatment or suppression of said diseases and associated aspects of the invention are described in more detail herein By "subject," "individual," or "patient" is meant an individual organism, preferably a vertebrate, more preferably a mammal, most preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. Because many of the mitochondrial disorders are inherited, genetic screening can be used to identify patients at risk of the disease. The compounds and methods of the invention can then be administered to asymptomatic patients at risk of developing the clinical symptoms of the disease, in order to suppress the appearance of any adverse symptoms. "Therapeutic use" of the compounds discussed herein is defined as using one or more of the compounds discussed herein to treat or suppress a disease, as defined above. An "effective amount" of a compound is an amount of the compound sufficient to modulate, normalize, or enhance one or more energy biomarkers (where modulation, normalization, and enhancement are defined below). A "therapeutically effective amount" of a compound is an amount of the compound, which, when administered to a subject, is sufficient to reduce or eliminate either a disease or one or more symptoms of a disease, or to retard the progression of a disease or of one or more symptoms of a disease, or to reduce the severity of a disease or of one or more symptoms of a disease, or to suppress the clinical manifestation of a disease, or to suppress the manifestation of adverse symptoms of a disease. A therapeutically effective amount can be given in one or more administrations. An "effective amount" of a compound embraces both a therapeutically effective amount, as well as an amount effective to modulate, normalize, or enhance one or more energy biomarkers in a subject.

"Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and enhancement as defined below.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. That is, to normalize an energy biomarker which is depressed in a disease state means to increase the level of the energy biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. For example, in a situation where significant energy demands are placed on a subject, it may be desirable to increase the level of ATP in that subject to a level above the normal level of ATP in that subject. Enhancement can also be of beneficial effect in a subject suffering from a disease or pathology such as a mitochondrial disease, in that normalizing an energy biomarker may not achieve the optimum outcome for the subject; in such cases, enhancement of one or more energy biomarkers can be beneficial, for example, higher-than-normal levels of ATP, or lower-than-normal levels of lactic acid (lactate) can be beneficial to such a subject.

By modulating, normalizing, or enhancing the energy biomarker Coenzyme Q is meant modulating, normalizing, or enhancing the variant or variants of Coenzyme Q which is predominant in the species of interest. For example, the variant of Coenzyme Q which predominates in humans is Coenzyme Q10. If a species or subject has more than one variant of Coenzyme Q present in significant amounts (i.e., present in amounts which, when modulated, normalized, or enhanced, can have a beneficial effect on the species or subject), modulating, normalizing, or enhancing Coenzyme Q can refer to modulating, normalizing or enhancing any or all variants of Coenzyme Q present in the species or subject.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared.

The invention also includes, if chemically possible, all stereoisomers of the compounds, including diastereomers and enantiomers. The invention also includes mixtures of possible stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds, which are themselves relatively inactive but which convert into the active compound when introduced into the subject in which they are used by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, Design of Prodrugs, New York: Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

Metabolites of the compounds are also embraced by the invention.

"$(C_1-C_6)$ alkyl" is intended to embrace a saturated linear, branched, or cyclic hydrocarbon, or any combination thereof, of 1 to 6 carbon atoms. Examples of "$(C_1-C_6)$ alkyl" are methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl, cyclopentyl, hexyl, and cyclohexyl. The point of attachment of the $(C_1-C_6)$ alkyl group to the remainder of the molecule can be at any chemically possible location on the $(C_1-C_6)$ alkyl group.

"$(C_2-C_6)$-alkenyl" is intended to embrace an unsaturated linear, branched, or cyclic group, or any combination thereof, having 2 to 6 carbon atoms. All double bonds may be independently either (E) or (Z) geometry, as well as arbitrary mixtures thereof. Examples of alkenyl groups include, but are not limited to —$CH_2$—CH=CH—$CH_3$; and —$CH_2$—$CH_2$-cyclohexenyl, where the ethyl group can be attached to the cyclohexenyl moiety at any available carbon valence.

"$(C_2-C_6)$-alkynyl" is intended to embrace an unsaturated linear, branched, or cyclic group, or any combination thereof, having 2 to 6 carbon atoms, which contain at least one triple bond.

"Halogen" or "halo" designates fluoro, chloro, bromo, and iodo.

"$(C_1-C_6)$ haloalkyl" is intended to embrace any $C_1-C_6$ alkyl substituent having at least one halogen substituent; the halogen can be attached via any valence on the $C_1-C_6$ alkyl group. Some examples of $C_1-C_6$ haloalkyl are —$CF_3$, —$CCl_3$, —$CHCl_2$, —$CHBr_2$, —$CH_2F$, —$CH_2Cl$, or —$CF_2CF_3$.

The term "aryl" is intended to embrace an aromatic cyclic hydrocarbon group of from 6 to 20 carbon atoms having a single ring (e.g., phenyl) or multiple condensed (fused) rings (e.g., naphthyl or anthryl).

The terms "heterocycle", "heterocyclic", "heterocyclo", and "heterocyclyl" is intended to encompass a monovalent saturated, partially unsaturated, or unsaturated carbocyclic radical having one or more rings incorporating one, two, three or four heteroatoms within the ring (chosen from nitrogen, oxygen, and/or sulfur). Examples of heterocycles include morpholine, piperidine, piperazine, thiazolidine, pyrazolidine, pyrazoline, imidazolidine, pyrrolidine, tetrahydropyran, tetrahydrofuran, quinuclidine, and the like. This term also includes heteroaryl groups as described below.

For "optionally substituted heterocyclyl," substituents can include $(C_1-C_6)$-alkyl, halo$(C_1-C_6)$haloalkyl, halogen, amino, nitro, cyano, aryl, aralkyl, heterocyclyl, —C(O)($C_1$-$C_6$)alkyl, —C(O)aryl, —C(O)heterocyclyl, —C(O)($C_1$-$C_8$)cycloalkyl, —C(O)OH, —C(O)O($C_1$-$C_6$)-alkyl, —C(O)O-aralkyl, —C(O)O-aryl, —C(O)NH2, —C(O)NH($C_1$-$C_6$)-alkyl, —C(O)N(($C_1$-$C_6$)-alkyl)$_2$, —C(O)NH-aryl, —NHC(O)($C_1$-$C_6$)-alkyl, —N(($C_1$-$C_6$)-alkyl)-C(O)($C_1$-$C_6$)-alkyl, —NHC(O)aryl, —N(($C_1$-$C_6$)-alkyl)-C(O)aryl, —C(O)NH($C_1$-$C_6$)-alkyl, —C(O)N(($C_1$-$C_6$)-alkyl)$_2$, —C(O)NH-aryl, —NHS(O)$_2$($C_1$-$C_6$)-alkyl, —N(($C_1$-$C_6$)-alkyl)-S(O)$_2$($C_1$-$C_6$)-alkyl, —NHS(O)$_2$-aryl, —N(($C_1$-$C_6$)-alkyl)-S(O)$_2$-aryl, —S(O)$_2$NH($C_1$-$C_6$)-alkyl, —S(O)$_2$N(($C_1$-$C_6$)-alkyl)$_2$, —S(O)$_2$NH-aryl, or oxo.

The terms "heteroaryl", is intended to encompass a monovalent aromatic, carbocyclic radical having one or more rings incorporating one, two, three or four heteroatoms within the ring (chosen from nitrogen, oxygen, and/or sulfur). Examples of heteroaryl include pyridine, pyrazine, imidazoline, thiazole, isothiazole, pyrazine, triazine, pyrimidine, pyridazine, pyrazole, thiophene, pyrrole, pyran, furan, indole, quinoline, quinazoline, benzimidazole, benzothiophene, benzofuran, benzoxazole, benzothiazole, benzotriazole, imidazo-pyridines, pyrazolo-pyridines, pyrazolo-pyrazine, acridine, carbazole, isoindole, isoquinoline, indazole, cinnoline, quinazoline, quinoxaline, phthalazine, benzotriazole, imidazo-pyridine, pyrazolopyrazine, pyrazolo-pyridazine, tetrahydropurine, pyrimido-pyrimidine, pyrazino-pyridazines, dibenzazepine, phenanthridine, phenazine, benzisoxazole, benzoxazine, phenoxazine, benzothiazole, benzoisothiazole, benzothiazine, and the like.

The terms "Parkinson's", (also called "Parkinsonism" and "Parkinsonian syndrome") ("PD") is intended to include not only Parkinson's disease but also drug-induced Parkinsonism and post-encephalitic Parkinsonism. Parkinson's disease is also known as paralysis agitans or shaking palsy. It is characterized by tremor, muscular rigidity and loss of postural reflexes. The disease usually progresses slowly with intervals of 10 to 20 years elapsing before the symptoms cause incapacity. Due to their mimicry of effects of Parkinson's disease, treatment of animals with methamphetamine or MPTP has been used to generate models for Parkinson's disease. These animal models have been used to evaluate the efficacy of various therapies for Parkinson's disease.

By "respiratory chain disorder" is meant a disorder which results in the decreased utilization of oxygen by a mitochondrion, cell, tissue, or individual, due to a defect or disorder in a protein or other component contained in the mitochondrial respiratory chain. By "protein or other component contained in the mitochondrial respiratory chain" is meant the components (including, but not limited to, proteins, tetrapyrroles, and cytochromes) comprising mitochondrial complex I, II, III, IV, and/or V. "Respiratory chain protein" refers to the protein components of those complexes, and "respiratory chain protein disorder" is meant a disorder which results in the decreased utilization of oxygen by a mitochondrion, cell, tissue, or individual, due to a defect or disorder in a protein contained in the mitochondrial respiratory chain.

The term "Friedreich's ataxia" is intended to embrace other related ataxias, and is also sometimes referred to as hereditary ataxia, familial ataxia, or Friedreich's tabes.

The term "ataxia" is an aspecific clinical manifestation implying dysfunction of parts of the nervous system that coordinate movement, such as the cerebellum. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias. Ataxias are also often associated with hearing impairments.

There are three types of ataxia, cerebellar ataxia, including vestibulo-cerebellar dysfunction, spino-cerebellar dysfunction, and cerebro-cerebellar dysfunction; sensory ataxia; and vestibular ataxia. Examples of the diseases which are classifiable into spino-cerebellar ataxia or multiple system atrophy are hereditary olivo-ponto-cerebellar atrophy, hereditary cerebellar cortical atrophy, Friedreich's ataxia, Machado-Joseph diseases, Ramsay Hunt syndrome, hereditary dentatorubral-pallidoluysian atrophy, hereditary spastic paraplegia, Shy-Drager syndrome, cortical cerebellar atrophy, striato-nigral degeneration, Marinesco-Sjogren syndrome, alcoholic cortical cerebellar atrophy, paraneoplastic cerebellar atrophy associated with malignant tumor, toxic cerebellar atrophy caused by toxic substances, cerebellar atrophy associated with endocrine disturbance and the like.

Examples of ataxia symptoms are motor ataxia, trunk ataxia, limb ataxia and the like, autonomic disturbance such as orthostatic hypotension, dysuria, hypohidrosis, sleep apnea, orthostatic syncope and the like, stiffness of lower extremity, ocular nystagmus, oculomotor nerve disorder, pyramidal tract dysfunction, extrapyramidal symptoms (postural adjustment dysfunction, muscular rigidity, akinesia, tremors), dysphagia, lingual atrophy, posterior funiculus symptom, muscle atrophy, muscle weakness, deep hyperreflexia, sensory disturbance, scoliosis, kyphoscoliosis, foot deformities, anarthria, dementia, manic state, decreased motivation for rehabilitation and the like.

Diseases Amenable to Treatment or Suppression with Compounds and Methods of the Invention A variety of diseases are believed to be caused or aggravated by oxidative stress affecting normal electron flow in the cells, such as mitochondrial disorders, impaired energy processing disorder, neurodegenerative diseases and diseases of aging, and can be treated or suppressed using the compounds and methods of the invention. Such diseases include, but are not limited to, inherited mitochondrial diseases, such as Myoclonic Epilepsy with Ragged Red Fibers (MERRF), Mitochondrial Myopathy, Encephalopathy, Lactacidosis, and Stroke (MELAS), Leber's Hereditary Optic Neuropathy (LHON, also referred to as Leber's Disease, Leber's Optic Atrophy (LOA), or Leber's Optic Neuropathy (LON)), Leigh Disease or Leigh Syndrome, Kearns-Sayre Syndrome (KSS), Friedreich's Ataxia (FA), CoQ10 Deficiency; other myopathies (including cardiomyopathy and encephalomyopathy), and renal tubular acidosis; neurodegenerative diseases, such as Parkinson's disease, Alzheimer's disease, amyotrophic lateral sclerosis (ALS, also known as Lou Gehrig's disease), motor neuron diseases; other neurological diseases such as epilepsy; genetic diseases such as Huntington's Disease (which is also a neurological disease); mood disorders such as schizophrenia and bipolar disorder; cerebral vascular accidents such as stroke, and certain age-associated diseases, particularly diseases for which CoQ10 has been proposed for treatment, such as macular degeneration, diabetes, and cancer. Mitochondrial dysfunction is also implicated in excitotoxic, neuronal injury, such as that associated with seizures, stroke and ischemia. Diseases caused by energy impairment include diseases due to deprivation, poisoning or toxicity of oxygen, and qualitative or quantitative disruption in the transport of oxygen such as haemoglobionopathies, for example thalassemia or sickle cell anemia.

Vision impairments amenable to treatment with the compounds and methods of the invention include, but are not limited to, vision impairments caused by neurodegenerative diseases of the eye such as optic neuropathy, Leber's hereditary optic neuropathy, dominant inherited juvenile optic atrophy, optic neuropathy caused by toxic agents, glaucoma, age-related macular degeneration (both "dry" or non-exudative macular degeneration and "wet" or exudative macular degeneration), Stargardt's macular dystrophy, diabetic retinopathy, diabetic maculopathy, retinopathy of prematurity, or ischemic reperfusion-related retinal injury.

For some diseases amenable to treatment with compounds and methods of the invention, the primary cause of the disease is due to a defect in the respiratory chain or another defect preventing normal utilization of energy in mitochondria, cells, or tissue(s). Examples of diseases falling in this category are inherited mitochondrial diseases, such as Myoclonic Epilepsy with Ragged Red Fibers (MERRF), Mitochondrial Myopathy, Encephalopathy, Lactacidosis, and Stroke (MELAS), Leber's Hereditary Optic Neuropathy (LHON, also referred to as Leber's Disease, Leber's Optic Atrophy (LOA), or Leber's Optic Neuropathy (LON)), Leigh Disease or Leigh Syndrome, Kearns-Sayre Syndrome (KSS), and Friedreich's Ataxia (FA). For other diseases amenable to treatment with compounds and methods of the invention, the primary cause of the disease is not due to respiratory chain defects or other defects preventing normal utilization of energy in mitochondria, cells, or tissue(s); examples of diseases falling in this category include stroke, cancer, and diabetes. However, these latter diseases are particularly aggravated by energy impairments, and are particularly amenable to treatment with compounds of the invention in order to ameliorate the condition. Pertinent examples of such diseases include ischemic stroke and hemorrhagic stroke, where the primary cause of the disease is due to impaired blood supply to the brain. While an ischemic episode caused by a thrombosis or embolism, or a hemorrhagic episode caused by a ruptured blood vessel, is not primarily caused by a defect in the respiratory chain or another metabolic defect preventing normal utilization of energy, oxidative stress plays a role in the ischemic cascade due to oxygen reperfusion injury following hypoxia (this cascade occurs in heart attacks as well as in strokes). Accordingly, treatment with compounds and methods of the invention will mitigate the effects of the disease, disorder or condition. Modulating one or more energy biomarkers, normalizing one or more energy biomarkers, or enhancing one or more energy biomarkers can also prove beneficial in such diseases both as a therapeutic measure and a prophylactic area. For example, for a patient scheduled to undergo non-emergency repair of an aneurysm, enhancing energy biomarkers before and during the pre-operative can improve the patient's prognosis should the aneurysm rupture before successful repair.

The terms "oxidative stress disorder" or "oxidative stress disease" encompass both diseases caused by oxidative stress and diseases aggravated by oxidative stress. The terms "oxidative stress disorder" or "oxidative stress disease" encompass both diseases and disorders where the primary cause of the disease is due to a defect in the respiratory chain or another defect preventing normal utilization of energy in mitochondria, cells, or tissue(s), and also diseases and disorders where the primary cause of the disease is not due to a defect in the respiratory chain or another defect preventing normal utilization of energy in mitochondria, cells, or tissue (s). The former set of diseases can be referred to as "primary oxidative stress disorders," while the latter can be referred to as "secondary oxidative stress disorders." It should be noted that the distinction between "diseases caused by oxidative stress" and "diseases aggravated by oxidative stress" is not absolute; a disease may be both a disease caused by oxidative stress and a disease aggravated by oxidative stress. The boundary between "primary oxidative stress disorder" and a "secondary oxidative stress disorder" is more distinct, provided that there is only one primary cause of a disease or disorder and that primary cause is known.

Bearing in mind the somewhat fluid boundary between diseases caused by oxidative stress and diseases aggravated by oxidative stress, mitochondrial diseases or disorders and impaired energy processing diseases and disorders tend to fall into the category of diseases caused by oxidative stress, while neurodegenerative disorders and diseases of aging tend to fall into the category of diseases aggravated by oxidative stress. Mitochondrial diseases or disorders and impaired energy processing diseases and disorders are generally primary oxidative stress disorders, while neurodegenerative disorders and diseases of aging may be primary or secondary oxidative stress disorders.

Clinical Assessment of Mitochondrial Dysfunction and Efficacy of Therapy

Several readily measurable clinical markers are used to assess the metabolic state of patients with mitochondrial disorders or impaired energy processing disorders. These markers can also be used as indicators of the efficacy of a given therapy, as the level of a marker is moved from the pathological value to the healthy value. These clinical markers include, but are not limited to, energy biomarkers such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+H$^+$) or NADPH (NADPH+H$^+$) levels; NAD or NADP levels; ATP levels; anaerobic threshold; reduced coenzyme Q (CoQ$^{red}$) levels; oxidized coenzyme Q (CoQ$^{ox}$) levels; total coenzyme Q (CoQ$^{tot}$) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment of the invention, the level of one or more energy biomarkers in a patient suffering from a mitochondrial disease, such as Friedreich's ataxia, Leber's hereditary optic neuropathy, MELAS, KSS or CoQ10 deficiency, is improved to within two standard deviations of the average level in a healthy subject. In another embodiment of the invention, the level of one or more of these energy biomarkers in a patient suffering from a mitochondrial disease, such as Friedreich's ataxia, Leber's hereditary optic neuropathy, MELAS, KSS or CoQ10 deficiency is improved to within one standard deviation of the average level in a healthy subject. Exercise intolerance can also be used as an indicator of the efficacy of a given therapy, where an improvement in exercise tolerance (i.e., a decrease in exercise intolerance) indicates efficacy of a given therapy.

Several metabolic biomarkers have already been used to evaluate efficacy of CoQ10, and these metabolic biomarkers can be monitored as energy biomarkers for use in the methods of the current invention. Pyruvate, a product of the anaerobic metabolism of glucose, is removed by reduction to lactic acid in an anaerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/ pyruvate ratio (Chariot et al., Arch. Pathol. Lab. Med. 118(7): 695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4): 448-55 (1992)) and toxic mitochondrial myopathies (Chariot et al., Arthritis Rheum. 37(4):583-6 (1994)). Changes in the redox state of liver mitochondria can be investigated by measuring the arterial ketone body ratio (acetoacetate/3-hydroxybutyrate: AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2): 287-91 (1997); Honda et al., Leuk. Res. 24(6):461-8 (2000); Pilger et al., Free Radic. Res. 35(3):273-80 (2001); Kim et al. Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., Neurology 62(8):1297-302 (2004)). Phosphorous MRS (31P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann Neurol. 29(4):435-8 (1991); Barbiroli et al., J. Neurol. 242 (7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-VO2 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic Acid (Lactate) Levels:

Mitochondrial dysfunction typically results in abnormal levels of lactic acid, as pyruvate levels increase and pyruvate is converted to lactate to maintain capacity for glycolysis. Mitochondrial dysfunction can also result in abnormal levels of $NADH+H^+$, $NADPH+H^+$, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, NADH ($NADH+H^+$) or NADPH ($NADPH+H^+$) can be measured by a variety of fluorescent, enzymatic, or electrochemical techniques, e.g., the electrochemical assay described in US 2005/0067303.

Oxygen Consumption ($vO_2$ or VO2), Carbon Dioxide Output ($vCO_2$ or VCO2), and Respiratory Quotient (VCO2/VO2):

$vO_2$ is usually measured either while resting (resting $vO_2$) or at maximal exercise intensity ($vO_2$ max). Optimally, both values will be measured. However, for severely disabled patients, measurement of $vO_2$ max may be impractical. Measurement of both forms of $vO_2$ is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, Reduced Cytochrome C, and Ratio of Oxidized Cytochrome C to Reduced Cytochrome C:

Cytochrome C parameters, such as oxidized cytochrome C levels (Cyt $C_{ox}$), reduced cytochrome C levels (Cyt $C_{red}$), and the ratio of oxidized cytochrome C/reduced cytochrome C ratio (Cyt $C_{ox}$/(Cyt $C_{red}$), can be measured by in vivo near infrared spectroscopy. See, e.g., Rolfe, P., "In vivo near-infrared spectroscopy," Annu. Rev. Biomed. Eng. 2:715-54 (2000) and Strangman et al., "Non-invasive neuroimaging using near-infrared light" Biol. Psychiatry 52:679-93 (2002).

Exercise Tolerance/Exercise Intolerance:

Exercise intolerance is defined as "the reduced ability to perform activities that involve dynamic movement of large skeletal muscles because of symptoms of dyspnea or fatigue" (Piña et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q ($CoQ^{red}$) levels, oxidized coenzyme Q ($CoQ^{ox}$) levels, total coenzyme Q ($CoQ^{tot}$) levels, oxidized cytochrome C levels, reduced cytochrome C levels, oxidized cytochrome C/reduced cytochrome C ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to evaluate efficacy of the compounds and methods of the invention. (For the purposes of the invention, modulation, normalization, or enhancement of energy biomarkers includes modulation, normalization, or enhancement of anaerobic threshold.)

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods of the invention. RQ=respiratory quotient; BMR=basal metabolic rate; HR (CO)=heart rate (cardiac output); T=body temperature (preferably measured as core temperature); AT=anaerobic threshold; pH=blood pH (venous and/or arterial).

TABLE 1

| Site of Dysfunction | Biochemical Event | Measurable Energy Biomaker | Physical Effect |
| --- | --- | --- | --- |
| Respiratory Chain | ↑ NADH | Δ lactate, Δ lactate: pyruvate ratio; and Δ acetoacetate: β-hydroxy butyrate ratio | Metabolic dyscrasia & fatigue |
| Respiratory Chain | ↓ $H^+$ gradient | Δ ATP | Organ dependent dysfunction |

TABLE 1-continued

| Site of Dysfunction | Biochemical Event | Measurable Energy Biomaker | Physical Effect |
|---|---|---|---|
| Respiratory Chain | ↓ Electron flux | Δ $VO_2$, RQ, BMR, ΔT, ΔT pH, | Metabolic dyscrasia & fatigue |
| Mitochondria & cytosol | ↓ ATP, ↓ $VO_2$ | Δ Work, ΔHR (CO) | Exercise intolerance |
| Mitochondria & cytosol | ↓ ATP | Δ PCr | Exercise intolerance |
| Respiratory Chain | ↓ Cyt $C_{Ox/Red}$ | Δ λ ~700-900 nm (Near Infrared Spectroscopy) | Exercise intolerance |
| Intermediary metabolism | ↓ Catabolism | Δ $C^{14}$-Labeled substrates | Metabolic dyscrasia & fatigue |
| Respiratory Chain | ↓ Electron flux | Δ Mixed Venous $VO_2$ | Metabolic dyscrasia & fatigue |
| Mitochondria & cytosol | ↑ Oxidative stress | Δ Tocopherol & Tocotrienols, CoQ10, docosahexaenoic acid | Uncertain |
| Mitochondria & cytosol | ↑ Oxidative stress | Δ $Glutathione_{red}$ | Uncertain |
| Mitochondria & cytosol | Nucleic acid oxidation | Δ8-hydroxy 2-deoxy guanosine | Uncertain |
| Mitochondria & cytosol | Lipid oxidation | Δ Isoprostane(s) eicosanoids | Uncertain |
| Cell membranes | Lipid oxidation | Δ Ethane (breath) | Uncertain |
| Cell membranes | Lipid oxidation | Δ Malondialdehyde | Uncertain |

Treatment of a subject afflicted by a mitochondrial disease in accordance with the methods of the invention may result in the inducement of a reduction or alleviation of symptoms in the subject, e.g., to halt the further progression of the disorder.

Partial or complete suppression of the mitochondrial disease can result in a lessening of the severity of one or more of the symptoms that the subject would otherwise experience. For example, partial suppression of MELAS could result in reduction in the number of stroke-like or seizure episodes suffered.

Any one or any combination of the energy biomarkers described herein provide conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

Use of Compounds for Modulation of Energy Biomarkers

In addition to monitoring energy biomarkers to assess the status of treatment or suppression of mitochondrial diseases or impaired energy processing disorders, the compounds of the invention can be used in subjects or patients to modulate one or more energy biomarkers. Modulation of energy biomarkers can be done to normalize energy biomarkers in a subject, or to enhance energy biomarkers in a subject.

Normalization of one or more energy biomarkers is defined as either restoring the level of one or more such energy biomarkers to normal or near-normal levels in a subject whose levels of one or more energy biomarkers show pathological differences from normal levels (i.e., levels in a healthy subject), or to change the levels of one or more energy biomarkers to alleviate pathological symptoms in a subject. Depending on the nature of the energy biomarker, such levels may show measured values either above or below a normal value. For example, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of energy biomarkers can involve restoring the level of energy biomarkers to within about at least two standard deviations of normal in a subject, more preferably to within about at least one standard deviation of normal in a subject, to within about at least one-half standard deviation of normal, or to within about at least one-quarter standard deviation of normal.

Enhancement of the level of one or more energy biomarkers is defined as changing the extant levels of one or more energy biomarkers in a subject to a level which provides beneficial or desired effects for the subject. For example, a person undergoing strenuous effort or prolonged vigorous physical activity, such as mountain climbing, could benefit from increased ATP levels or decreased lactate levels. As described above, normalization of energy biomarkers may not achieve the optimum state for a subject with a mitochondrial disease, and such subjects can also benefit from enhancement of energy biomarkers. Examples of subjects who could benefit from enhanced levels of one or more energy biomarkers include, but are not limited to, subjects undergoing strenuous or prolonged physical activity, subjects with chronic energy problems, or subjects with chronic respiratory problems. Such subjects include, but are not limited to, pregnant females, particularly pregnant females in labor; neonates, particularly premature neonates; subjects exposed to extreme environments, such as hot environments (temperatures routinely exceeding about 85-86 degrees Fahrenheit or about 30 degrees Celsius for about 4 hours daily or more), cold environments (temperatures routinely below about 32 degrees Fahrenheit or about 0 degrees Celsius for about 4 hours daily or more), or environments with lower-than-average oxygen content, higher-than-average carbon dioxide content, or higher-than-average levels of air pollution (airline travelers, flight attendants, subjects at elevated altitudes, subjects living in cities with lower-than-average air quality, subjects working in enclosed environments where air quality is degraded); subjects with lung diseases or lower-than-average lung capacity, such as tubercular patients, lung cancer patients, emphysema patients, and cystic fibrosis patients; subjects recovering from surgery or illness; elderly subjects, including elderly subjects experiencing decreased energy; subjects suffering from chronic fatigue, including chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

Accordingly, when an increase in a level of one or more energy biomarkers is beneficial to a subject, enhancement of the one or more energy biomarkers can involve increasing the level of the respective energy biomarker or energy biomarkers to about at least one-quarter standard deviation above normal, about at least one-half standard deviation above normal, about at least one standard deviation above lumina', or about at least two standard deviations above normal. Alternatively, the level of the one or more energy biomarkers can be increased by about at least 10% above the subject's level of the respective one or more energy biomarkers before enhancement, by about at least 20% above the subject's level of the respective one or more energy biomarkers before enhancement, by about at least 30% above the subject's level of the respective one or more energy biomarkers before enhancement, by about at least 40% above the subject's level of the respective one or more energy biomarkers before enhancement, by about at least 50% above the subject's level of the respective one or more energy biomarkers before enhancement, by about at least 75% above the subject's level of the respective one or more energy biomarkers before enhancement, or by about at least 100% above the subject's level of the respective one or more energy biomarkers before enhancement.

When a decrease in a level of one or more energy biomarkers is desired to enhance one or more energy biomarkers, the level of the one or more energy biomarkers can be decreased by an amount of about at least one-quarter standard deviation of normal in a subject, decreased by about at least one-half standard deviation of normal in a subject, decreased by about at least one standard deviation of normal in a subject, or decreased by about at least two standard deviations of normal in a subject. Alternatively, the level of the one or more energy biomarkers can be decreased by about at least 10% below the subject's level of the respective one or more energy biomarkers before enhancement, by about at least 20% below the subject's level of the respective one or more energy biomarkers before enhancement, by about at least 30% below the subject's level of the respective one or more energy biomarkers before enhancement, by about at least 40% below the subject's level of the respective one or more energy biomarkers before enhancement, by about at least 50% below the subject's level of the respective one or more energy biomarkers before enhancement, by about at least 75% below the subject's level of the respective one or more energy biomarkers before enhancement, or by about at least 90% below the subject's level of the respective one or more energy biomarkers before enhancement.

Use of Compounds in Research Applications, Experimental Systems, and Assays

The compounds of the invention can also be used in research applications. They can be used in in vitro, in vivo, or ex vivo experiments to modulate one or more energy biomarkers in an experimental system. Such experimental systems can be cell samples, tissue samples, cell components or mixtures of cell components, partial organs, whole organs, or organisms. Any one or more of the compounds of formula I, Ia, and Ib, can be used in experimental systems or research applications. Such research applications can include, but are not limited to, use as assay reagents, elucidation of biochemical pathways, or evaluation of the effects of other agents on the metabolic state of the experimental system in the presence/absence of one or more compounds of the invention.

Additionally, the compounds of the invention can be used in biochemical tests or assays. Such tests can include incubation of one or more compounds of the invention with a tissue or cell sample from a subject to evaluate a subject's potential response (or the response of a specific subset of subjects) to administration of said one or more compounds, or to determine which compound of the invention produces the optimum effect in a specific subject or subset of subjects. One such test or assay would involve 1) obtaining a cell sample or tissue sample from a subject in which modulation of one or more energy biomarkers can be assayed; 2) administering one or more compounds of the invention to the cell sample or tissue sample; and 3) determining the amount of modulation of the one or more energy biomarkers after administration of the one or more compounds, compared to the status of the energy biomarker prior to administration of the one or more compounds. Another such test or assay would involve 1) obtaining a cell sample or tissue sample from a subject in which modulation of one or more energy biomarkers can be assayed; 2) administering at least two compounds of the invention to the cell sample or tissue sample; 3) determining the amount of modulation of the one or more energy biomarkers after administration of the at least two compounds, compared to the status of the energy biomarker prior to administration of the at least two compounds, and 4) selecting a compound or compounds for use in treatment, suppression, or modulation based on the amount of modulation determined in step 3.

Pharmaceutical Formulations

The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

The invention also provides articles of manufacture and kits containing materials useful for treating or suppressing oxidative stress diseases affecting normal electron flow in the cells, such as mitochondrial diseases, impaired energy processing disorders, neurodegenerative disorders and diseases of aging. The invention also provides kits comprising any one or more of the compounds of formulas I, Ia, and/or Ib. In some embodiments, the kit of the invention comprises the container described above.

In other aspects, the kits may be used for any of the methods described herein, including, for example, to treat an individual with a mitochondrial disorder, or to suppress a mitochondrial disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are a therapeutically effective amount or effective amount within the dosage range of about 0.1 mg/kg to about 300 mg/kg body weight, or within about 1.0 mg/kg to about 100 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Compounds of the present invention may be administered in a single daily dose, or the total daily dosage may be administered in divided dosage of two, three or four times daily.

While the compounds of the invention can be administered as the sole active pharmaceutical agent, they can also be used in combination with one or more other agents used in the treatment or suppression of disorders. Representative agents useful in combination with the compounds of the invention for the treatment or suppression of mitochondrial diseases include, but are not limited to, Coenzyme Q, vitamin E, idebenone, MitoQ, vitamins, and antioxidant compounds.

When additional active agents are used in combination with the compounds of the present invention, the additional active agents may generally be employed in therapeutic amounts as indicated in the Physicians' Desk Reference (PDR) 53rd Edition (1999), or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

The invention will be further understood by the following nonlimiting examples.

In general, the nomenclature used in this Application was generated with the help of naming package within the ChemOffice® version 11.0 suite of programs by Cambridge-Soft Corp (Cambridge, Mass.).

Preparation of Compounds of the Invention

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol ("MeOH"), acetone, water, acetonitrile, 1,4-dioxane, dimethylformamide ("DMF"), benzene, toluene, xylene, tetrahydrofuran ("THF"), chloroform, methylene chloride (or dichloromethane, ("DCM")), diethyl ether, pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

$^1$H and $^{13}$C NMR were obtained on a Varian Ultrashielded magnet at 400 MHz and 100 MHz respectively in deuterated solvents as noted. All spectra are referenced in ppm to either their residual solvent peak, as defined in Gottlieb, H. E. et. al; *J. Org. Chem.* 1997, 62, 7512-7515, or TMS at 0.00 ppm. The FIDs were processed using Varian VNMRJ software or ACD Version 11 1D NMR processor. IR spectra were obtained on a Perkin ELMER Spectrum 100 equipped with a LiTa detector using a PE Universal single bounce SeGe/Diamond ATR stage as neat samples. Melting points were obtained on an Optimelt MPA-100 in unsealed borosilicate glass tubes at 5° C./min. HPLC and HPLC/MS data were obtained on an Agilent 1100 LC system attached to both a Diode Array spectrophotometer (see below) and a HP 1956B mass using an Agilent ACPI/ES multimode source in mixed mode. The HPLC column was a Phenomenex Luna phenyl-hexyl 150 mm×4.6 mm 5 μm silica supported column eluting with water/acetonitrile containing 0.02% (v/v) formic acid. Spectra were processed with Agilent chemstation software. Chromatographic separation was carried out on a Teledyne-ISCO Combiflash Companion using ISCO Redisep pre-packaged columns.

The starting compound, e.g., 2,3,5-trimethylhydroquinone, is commercially available, e.g. from Aldrich Chemical Company, Milwaukee, Wis., or may be readily prepared by those skilled in the art using commonly employed methodology.

EXAMPLES

Synthesis of Compounds

Example 1

2,3,5-Trimethyl-6-(2-(4-(trifluoromethyl)pyridin-2-ylamino)ethyl)cyclohexa-2,5-diene-1,4-dione Step 1: 1,4-Bis(benzyloxy)-3,5,6-trimethylbenzene A solution of 2,3,5-trimethylhydroquinone (15.2 g, 100 mmol) in DMF (150 mL) was treated with BnBr (35.7 mL, 51.6 g, 300 mmol, 3 equiv.) and anhydrous $K_2CO_3$ (55.3 g, 400 mmol, 4 equiv.). The brown suspension was heated to 60° C. for 48 h at which time the reaction was judged incomplete by HPLC. Additional BnBr (37 mL, 300 mmol, 3 equiv.) and $K_2CO_3$ (50 g, 362 mmol, 3.6 equiv.) were added and heated to 60° C. for an additional 48 h. The reaction was cooled, filtered through Celite, the filter cake rinsed 2×100 mL EtOAc and the combined filtrates washed with 500 mL $H_2O$. The aqueous layer was extracted 4×250 mL EtOAc and concentrated at 80° C. by rotary evaporation. The brown residue was poured onto 300 mL water which precipitated a light brown solid and the resulting suspension stirred overnight. The brown solid was collected by filtration, washed with 2×50 mL H$_2$O and dried, yielding 26.8 g of 1,4-bis(benzyloxy)-3,5,6-trimethylbenzene as a brown solid $^1$H NMR (400 MHz, CDCl$_3$) d=7.50-7.34 (m, 10H), 6.64 (s, 1H), 5.03 (s, 2H), 4.74 (s, 2H), 2.30 (s, 3H), 2.25 (s, 3H), 2.20 (s, 3H) ppm.

Step 2
2-Bromo-1,4-bis(benzyloxy)-3,5,6-trimethylbenzene

In 100 mL dimethyl ether (DME) was dissolved 1,4-bis (benzyloxy)-3,5,6-trimethylbenzene prepared as in step 1 (5 g, 15.0 mmol) which was treated with a solution of Br$_2$ (0.85 mL, 16.5 mmol, 1.1 equiv.) in 10 mL DME (1.6 M) over ten minutes via a dropping funnel. The reaction was judged incomplete by HPLC. Additional Br$_2$ in DME (0.42 mL, 1.31 g, 8.19 mmol, 0.55 equiv.) was added and stirred overnight. A white solid precipitated from the solution during the night. The reaction was treated with 200 mL EtOAc, which dissolved the solid, and washed with H$_2$O until the aqueous washings were colorless (3×100 mL) The combined aqueous layers were back extracted with EtOAc (3×50 mL) and the combined organics washed 2×100 mL saturated NaCl, dried over Na$_2$SO$_4$ and concentrated to a brown solid. The solid was adsorbed onto silica and purified by flash chromatography (gradient elution 2-20% EtOAc/heptane) to give a yellow solid. The solid was suspended into heptane, stirred overnight, filtered and the filter cake rinsed with heptane. The resulting white powder was dried in vacuo and yielded 3.31 g of 2-bromo-1,4-bis(benzyloxy)-3,5,6-trimethylbenzene as a white powder. HPLC 97.8% at 215 nm, did not ionize; $^1$H NMR (400 MHz, CDCl3) d=7.57 (d, 2H), 7.48 (d, 2H), 7.44-7.36 (m, 6H), 4.87 (s, 2H), 4.74 (s, 2H), 2.41 (s, 3H), 2.24 (s, 3H), 2.20 (s, 3H) ppm.

Step 3:
2,5-Bis(benzyloxy)-3,4,6-trimethylbenzaldehyde

2-Bromo-1,4-bis(benzyloxy)-3,5,6-trimethylbenzene (5.002 g, 12.16 mmol) was dissolved into 25 mL toluene and 25 mL Et$_2$O and cooled to 0° C. To this stirred yellow solution was added 8.2 mL n-BuLi (1.6 M in hexanes, 12.76 mmol, 1.05 equiv.) over ten minutes to give a clear yellow solution. After 20 min at 0° C. the solution became cloudy. To this slightly cloudy solution was added DMF (3 mL, 40 mmol, 2.8 g) which clarified the solution instantly upon addition. After overnight stirring, 50 mL 20% aqueous NH$_4$Cl was added followed by 100 mL H$_2$O and 100 mL EtOAc. The layers were separated and the aqueous phase extracted 3×100 mL EtOAc and the combined organics washed 2×50 mL saturated aqueous NaCl, dried over Na$_2$SO$_4$ and concentrated to a yellow oil which solidified to give 2,5-bis(benzyloxy)-3,4,6-trimethylbenzaldehyde as a pale brown solid (3.90 g). MS M$^+$+H=361 m/z; $^1$H NMR (400 MHz, CDCl3) d=10.51 (s, 1H), 7.51-7.37 (m, 10H), 4.87 (s, 2H), 4.74 (s, 2H), 2.55 (s, 3H), 2.30 (s, 3H), 2.25 (s, 3H) ppm.

Step 4: 2-(2,5-Bis(benzyloxy)-3,4,6-trimethylphenyl) ethanamine 2,5-Bis(benzyloxy)-3,4,6-trimethylbenzaldehyde (3.2 g, 8.8 mmol, 1.0 equiv.) and ammonium acetate (815 mg, 10.6 mmol, 1.15 equiv.) were taken up in nitromethane (44 mL). The resulting solution was stirred at 80° C. for 1 hr, after which HPLC analysis indicated that the reaction was complete. The mixture was diluted in 100 mL ethyl acetate and washed twice with brine (30 mL). The organics were dried over anhydrous sodium sulfate, filtered, and concentrated in vacuo to give 3.2 g yellow solid 2,5-bis(benzyloxy)-(3,4,6-trimethyl)nitrostyrene, which was used without further purification. The solid intermediate was dissolved in 22 mL anhydrous THF and added dropwise to a slurry of lithium aluminum hydride (2.1 g, 50 mmol, 6 equiv.) stirring at 0° C. After 60 min, the addition was complete, and the mixture was warmed to reflux. The reaction stirred for an additional 18 hr, after which HPLC analysis indicated the presence of some intermediate products. At this time, the mixture was cooled to ambient temperature and a second portion of lithium aluminum hydride (700 mg) was added. Following 30 min at reflux, the reaction was deemed complete. The mixture was slowly poured into 200 mL 2.5 M sodium hydroxide stirring in an ice-water bath. The resulting slurry was stirred for 20 min, diluted with i-PrOAc (200 mL), and filtered. The organics were removed and the aqueous layer washed twice with 100 mL i-PrOAc. The combined organics were dried over anhydrous sodium sulfate, filtered, and concentrated in vacuo to give 3.3 g of 2-(2,5-bis(benzyloxy)-3,4,6-trimethylphenyl) ethanamine as a white solid. $^1$H-NMR (400 MHz, CD$_3$OD) 7.51-7.31 (m, 10H), 4.77 (s, 2H), 4.72 (s, 2H), 2.83 (m, 2H), 2.71 (m, 2H), 2.24 (s, 3H), 2.22 (s, 3H), 2.13 (s, 3H) ppm.

Step 5: 2,3,5-Trimethyl-6-(2-(4-(trifluoromethyl) pyridin-2-ylamino)ethyl)cyclohexa-2,5-diene-1,4-dione To a stirring solution of 2-(2,5-bis(benzyloxy)-3,4,6-trimethylphenyl) ethanamine (500 mg, 1.3 mmol) in DMSO (1 mL) was added 2-chloro-4-trifluoromethyl pyridine (256 mg, 2.0 mmol, 1.5 equiv.) and diisopropyl ethyl amine (578 µL, 3.3 mmol, 2.5 equiv.). The resulting solution was stirred at 100° C. for 12 hr, after which time HPLC analysis indicated that the reaction was complete. The mixture was brought to 80° C., water (3 mL) was added, and the resulting suspension was stirred for 30 min. The mixture was subsequently brought to ambient temperature and stirred for an additional 30 min, after which the solids were collected by filtration. After drying in vacuo, 750 mg crude brown solids were obtained containing the desired product. The crude material was taken up in trifluoroacetic acid (6 mL) and treated with thioanisole (393 µL, 3.35 mmol). After stirring at ambient temperature for 1 hour, HPLC analysis indicated that the reaction was complete. Volatiles were removed in vacuo and the residue was taken up in 25 mL ethyl acetate. The organic layer was washed with water, 1 M aqueous sodium bicarbonate, and brine (10 mL each), dried over anhydrous sodium sulfate, filtered, and concentrated in vacuo. The crude hydroquinone (450 mg) was dissolved in acetonitrile (7 mL) and cooled in an ice-water bath. To the stirring solution was added an aqueous solution of ceric ammonium nitrate (1.46 g, 7.6 mmol in 2 mL) in a dropwise fashion. The reaction was deemed complete by TLC analysis when approximately 90% of the reagent was added. At this point, the mixture was partitioned between ethyl acetate and brine (15 mL each), and the organic layer was removed. The remaining aqueous layer was made basic by addition of 10 mL 1 M aqueous sodium bicarbonate, and extracted with ethyl acetate (15 mL). The combined organic layers were dried over anhydrous sodium sulfate, filtered, and concentrated in vacuo to produce 500 mg brown oil. Purification by silica gel chromatography (gradient elution 0→35% ethyl acetate in heptane) afforded 2,3,5-trimethyl-6-(2-(4-(trifluoromethyl)pyridin-2-ylamino)ethyl)cyclohexa-2,5-diene-1,4-dione as a bright yellow solid (85 mg). $^1$H-NMR (400 MHz, CDCl$_3$) 8.15 (d, 1H), 6.76 (m, 2H), 3.49 (m, 2H), 2.86 (t, 2H), 2.08 (s, 3H), 2.01 (s, 6H). M$^+$=338.0.

The following compounds were prepared using an analogous procedure to that described in Example 1:

2,3,5-Trimethyl-6-(2-(6-(trifluoromethyl)pyridin-2-ylamino)ethyl)cyclohexa-2,5-diene-1,4-dione; $^1$H-NMR (400 MHz, $CDCl_3$) 7.50 (t, 1H), 6.90 (d, 1H), 6.57 (d, 1H), 4.83 (br t, 1H), 3.43 (q, 2H), 2.80 (t, 2H), 2.08 (s, 3H), 2.00 (s, 6H) ppm. $M^+$=338.0.

2,3,5-Trimethyl-6-(2-(5-(trifluoromethyl)pyridin-2-ylamino)ethyl)cyclohexa-2,5-diene-1,4-dione; $^1$H-NMR (400 MHz, $CDCl_3$) 10.6 (br s, 1H), 8.12 (s, 1H), 8.00 (d, 1H), 7.32 (d, 1H), 3.41 (br t, 2H), 2.80 (t, 2H), 2.07 (s, 3H), 1.99 (s, 6H) ppm. $M^+$=338.0.

2-(2-(5-Fluoropyrimidin-2-ylamino)ethyl)-3,5,6-trimethylcyclohexa-2,5-diene-1,4-dione $^1$H-NMR (400 MHz, $CDCl_3$) 8.08 (s, 2H), 5.24 (br t, 1H), 3.49 (q, 2H), 2.80 (t, 2H) 2.02 (s, 6H), 2.00 (s, 3H) ppm. $M^+$=289.0.

2-(2-(4-Fluoropyrimidin-2-ylamino)ethyl)-3,5,6-trimethylcyclohexa-2,5-diene-1,4-dione; $M^+$=289.0.

2,3,5-Trimethyl-6-(2-(pyridin-2-ylamino)ethyl)cyclohexa-2,5-diene-1,4-dione; $^1$H-NMR (400 MHz, $CDCl_3$) 10.3 (br s, 1H), 7.89 (t, 1H), 7.74 (d, 1H), 7.20 (d, 1H), 6.76 (t, 1H), 3.39 (m, 2H), 2.80 (t, 2H), 2.08 (s, 3H), 2.01 (s, 6H) ppm. $M^++H^+$=271.1.

2,3,5-Trimethyl-6-(2-(4-(trifluoromethyl)pyrimidin-2-ylamino)ethyl)cyclohexa-2,5-diene-1,4-dione; $^1$H-NMR (400 MHz, $CDCl_3$) 8.42 (br s, 1H), 6.80 (d, 1H), 5.80 (br s, 1H), 3.55 (q, 2H), 2.81 (t, 2H), 2.07 (s, 3H), 2.01 (s, 6H) ppm. $M^++H^+$=340.1.

2,3,5-Trimethyl-6-(2-(pyrimidin-2-ylamino)ethyl)cyclohexa-2,5-diene-1,4-dione; $^1$H-NMR (400 MHz, $CDCl_3$) 8.23 (m, 2H), 6.52 (m, 1H), 5.21 (m, 1H), 3.56 (q, 2H), 2.81 (t, 2H), 2.01 (m, 9H) ppm. $M^++H^+$=272.2.

2,3,5-Trimethyl-6-(2-(3-(trifluoromethyl)pyridin-2-ylamino)ethyl)cyclohexa-2,5-diene-1,4-dione; $^1$H-NMR (400 MHz, $CDCl_3$) 8.22 (d, 1H), 7.62 (m, 1H), 6.60 (q, 1H), 3.61 (q, 2H), 2.87 (t, 2H), 2.03 (m, 6H), 2.01 (s, 3H) ppm. $M^++H^+$=339.0.

BIOLOGICAL EXAMPLES

Example A

Screening Compounds of the Invention in Human Dermal Fibroblasts from Friedreich's Ataxia Patients An initial screen was performed to identify compounds effective for the amelioration of redox disorders. Test samples, 4 reference compounds (idebenone, decylubiquinone, Trolox and α-tocopherol acetate), and solvent controls were tested for their ability to rescue FRDA fibroblasts stressed by addition of L-buthionine-(S,R)-sulfoximine (BSO), as described in Jauslin et al., Hum. Mol. Genet. 11(24):3055 (2002), Jauslin et al., FASEB J. 17:1972-4 (2003), and International Patent Application WO 2004/003565. Human dermal fibroblasts from Friedreich's Ataxia patients have been shown to be hypersensitive to inhibition of the de novo synthesis of glutathione (GSH) with L-buthionine-(S,R)-sulfoximine (BSO), a specific inhibitor of GSH synthetase (Jauslin et al., Hum. Mol. Genet. 11(24):3055 (2002)). This specific BSO-mediated cell death can be prevented by administration of antioxidants or molecules involved in the antioxidant pathway, such as α-tocopherol, selenium, or small molecule glutathione peroxidase mimetics. However, antioxidants differ in their potency, i.e. the concentration at which they are able to rescue BSO-stressed FRDA fibroblasts.

MEM (a medium enriched in amino acids and vitamins, catalog no. 1-31F24-I) and Medium 199 (M199, catalog no. 1-21F22-I) with Earle's Balanced Salts, without phenol red, were purchased from Bioconcept. Fetal Calf Serum was obtained from PAA Laboratories. Basic fibroblast growth factor and epidermal growth factor were purchased from PeproTech. Penicillin-streptomycin-glutamine mix, L-buthionine (S,R)-sulfoximine, (+)-α-tocopherol acetate, decylubiquinone, and insulin from bovine pancreas were purchased from Sigma. Trolox (6-Hydroxy-2,5,7,8-tetramethylchromane-2-carboxylic acid) was obtained from Fluka. Idebenone was obtained from Chemo Iberica. Calcein AM was purchased from Molecular Probes. Cell culture medium was made by combining 125 ml M199 EBS, 50 ml Fetal Calf Serum, 100 U/ml penicillin, 100 µg/ml streptomycin, 2 mM glutamine, 10 µg/ml insulin, 10 ng/ml EGF, and 10 ng/ml bFGF; MEM EBS was added to make the volume up to 500 ml. A 10 mM BSO solution was prepared by dissolving 444 mg BSO in 200 ml of medium (Invitrogen, Carlsbad, Ca.) with subsequent filter-sterilization. During the course of the experiments, this solution was stored at +4° C. The cells were obtained from the Coriell Cell Repositories (Camden, N.J.; repository number GM04078) and grown in 10 cm tissue culture plates. Every third day, they were split at a 1:3 ratio.

The test samples were supplied in 1.5 ml glass vials. The compounds were diluted with DMSO, ethanol or PBS to result in a 5 mM stock solution. Once dissolved, they were stored at −20° C. Reference antioxidants (idebenone, decylubiquinone, α-tocopherol acetate and Trolox) were dissolved in DMSO.

Test samples were screened according to the following protocol: A culture with FRDA fibroblasts was started from a 1 ml vial with approximately 500,000 cells stored in liquid nitrogen. Cells were propagated in 10 cm cell culture dishes by splitting every third day in a ratio of 1:3 until nine plates were available. Once confluent, fibroblasts were harvested. For 54 micro titer plates (96 well-MTP) a total of 14.3 million cells (passage eight) were re-suspended in 480 ml medium, corresponding to 100 µl medium with 3,000 cells/well. The remaining cells were distributed in 10 cm cell culture plates (500,000 cells/plate) for propagation. The plates were incubated overnight at 37° C. in a atmosphere with 95% humidity and 5% $CO_2$ to allow attachment of the cells to the culture plate.

MTP medium (243 µl) was added to a well of the microtiter plate. The test compounds were unfrozen, and 7.5 µl of a 5 mM stock solution was dissolved in the well containing 243 µl medium, resulting in a 150 µM master solution. Serial dilutions from the master solution were made. The period between the single dilution steps was kept as short as possible (generally less than 1 second).

Plates were kept overnight in the cell culture incubator. The next day, 10 µl of a 10 mM BSO solution were added to the wells, resulting in a 1 mM final BSO concentration. Forty-eight hours later, three plates were examined under a phase-contrast microscope to verify that the cells in the 0% control (wells E1-H1) were clearly dead. The medium from all plates was discarded, and the remaining liquid was removed by gently tapping the plate inversed onto a paper towel.

100 µl of PBS containing 1.2 µM Calcein AM were then added to each well. The plates were incubated for 50-70 minutes at room temperature. After that time the PBS was discarded, the plate gently tapped on a paper towel and fluorescence (excitation/emission wavelengths of 485 nm and 525 nm, respectively) was read on a Gemini fluorescence reader. Data was imported into Microsoft Excel (EXCEL is a registered trademark of Microsoft Corporation for a spreadsheet program) and used to calculate the EC$_{50}$ concentration for each compound.

The compounds were tested three times, i.e., the experiment was performed three times, the passage number of the cells increasing by one with every repetition.

The solvents (DMSO, ethanol, PBS) neither had a detrimental effect on the viability of non-BSO treated cells nor did they have a beneficial influence on BSO-treated fibroblasts even at the highest concentration tested (1%). None of the compounds showed auto-fluorescence. The viability of non-BSO treated fibroblasts was set as 100%, and the viability of the BSO- and compound-treated cells was calculated as relative to this value.

The following table summarizes the EC$_{50}$ for the four control compounds.

| Compound | EC$_{50}$ [μM] | | | | |
|---|---|---|---|---|---|
| | Value 1 | Value 2 | Value 3 | Average | Stdev |
| decylubiquinone | 0.05 | 0.035 | 0.03 | 0.038 | 0.010 |
| alpha-tocopherol acetate | 0.4 | 0.15 | 0.35 | 0.30 | 0.13 |
| Idebenone | 1.5 | 1 | 1 | 1.2 | 0.3 |
| Trolox | 9 | 9 | 8 | 8.7 | 0.6 |

Certain compounds of the present invention such as:
2,3,5-trimethyl-6-(2-(pyrimidin-2-ylamino)ethyl)cyclohexa-2,5-diene-1,4-dione;
2,3,5-trimethyl-6-(2-(pyridin-2-ylamino)ethyl)cyclohexa-2,5-diene-1,4-dione;
2,3,5-trimethyl-6-(2-(4-(trifluoromethyl)pyrimidin-2-ylamino)ethyl)cyclohexa-2,5-diene-1,4-dione;
2,3,5-trimethyl-6-(2-(4-(trifluoromethyl)pyridin-2-ylamino)ethyl)cyclohexa-2,5-diene-1,4-dione;
2,3,5-trimethyl-6-(2-(5-(trifluoromethyl)pyridin-2-ylamino)ethyl)cyclohexa-2,5-diene-1,4-dione;
2,3,5-trimethyl-6-(2-(6-(trifluoromethyl)pyridin-2-ylamino)ethyl)cyclohexa-2,5-diene-1,4-dione;
2,3,5-trimethyl-6-(2-(3-(trifluoromethyl)pyridin-2-ylamino)ethyl)cyclohexa-2,5-diene-1,4-dione;
2-(2-(5-fluoropyrimidin-2-ylamino)ethyl)-3,5,6-trimethylcyclohexa-2,5-diene-1,4-dione; and
2-(2-(4-fluoropyrimidin-2-ylamino)ethyl)-3,5,6-trimethylcyclohexa-2,5-diene-1,4-dione;
exhibited protection against FRDA with an EC$_{50}$ of less than about 100 nM.

Example B

Screening Compounds of the Invention in Fibroblasts from Huntington's Patients

Compounds of the invention were tested using a screen similar to the one described in Example A, but substituting FRDA cells with Huntington's cells obtained from the Coriell Cell Repositories (Camden, N.J.; repository number GM 04281). The compounds were tested for their ability to rescue human dermal fibroblasts from Huntington's patients from oxidative stress.

Certain compounds of the present invention such as:
2,3,5-trimethyl-6-(2-(pyrimidin-2-ylamino)ethyl)cyclohexa-2,5-diene-1,4-dione;
2,3,5-trimethyl-6-(2-(pyridin-2-ylamino)ethyl)cyclohexa-2,5-diene-1,4-dione;
2,3,5-trimethyl-6-(2-(4-(trifluoromethyl)pyrimidin-2-ylamino)ethyl)cyclohexa-2,5-diene-1,4-dione;
2,3,5-trimethyl-6-(2-(4-(trifluoromethyl)pyridin-2-ylamino)ethyl)cyclohexa-2,5-diene-1,4-dione;
2,3,5-trimethyl-6-(2-(5-(trifluoromethyl)pyridin-2-ylamino)ethyl)cyclohexa-2,5-diene-1,4-dione;
2,3,5-tri methyl-6-(2-(6-(trifluoromethyl)pyridin-2-ylamino)ethyl)cyclohexa-2,5-diene-1,4-dione;
2,3,5-trimethyl-6-(2-(3-(trifluoromethyl)pyridin-2-ylamino)ethyl)cyclohexa-2,5-diene-1,4-dione;
2-(2-(5-fluoropyrimidin-2-ylamino)ethyl)-3,5,6-trimethylcyclohexa-2,5-diene-1,4-dione; and
2-(2-(4-fluoropyrimidin-2-ylamino)ethyl)-3,5,6-trimethylcyclohexa-2,5-diene-1,4-dione;
exhibited protection against Huntington's with an EC$_{50}$ of less than about 100 nM.

Example C

Screening Compounds of the Invention in Fibroblasts from Leber's Hereditary Optic Neuropathy Patients Compounds of the invention were tested using a screen similar to the one described in Example A, but substituting FRDA cells with Leber's Hereditary Optic Neuropathy (LHON) cells obtained from the Coriell Cell Repositories (Camden, N.J.; repository number GM03858). The compounds were tested for their ability to rescue human dermal fibroblasts from LHON patients from oxidative stress.

Certain compounds of the present invention such as:
2,3,5-trimethyl-6-(2-(pyrimidin-2-ylamino)ethyl)cyclohexa-2,5-diene-1,4-dione;
2,3,5-trimethyl-6-(2-(pyridin-2-ylamino)ethyl)cyclohexa-2,5-diene-1,4-dione;
2,3,5-trimethyl-6-(2-(4-(trifluoromethyl)pyrimidin-2-ylamino)ethyl)cyclohexa-2,5-diene-1,4-dione;
2,3,5-trimethyl-6-(2-(4-(trifluoromethyl)pyridin-2-ylamino)ethyl)cyclohexa-2,5-diene-1,4-dione;
2,3,5-trimethyl-6-(2-(5-(trifluoromethyl)pyridin-2-ylamino)ethyl)cyclohexa-2,5-diene-1,4-dione;
2,3,5-trimethyl-6-(2-(6-(trifluoromethyl)pyridin-2-ylamino)ethyl)cyclohexa-2,5-diene-1,4-dione;
2,3,5-trimethyl-6-(2-(3-(trifluoromethyl)pyridin-2-ylamino)ethyl)cyclohexa-2,5-diene-1,4-dione;
2-(2-(5-fluoropyrimidin-2-ylamino)ethyl)-3,5,6-trimethylcyclohexa-2,5-diene-1,4-dione; and
2-(2-(4-fluoropyrimidin-2-ylamino)ethyl)-3,5,6-trimethylcyclohexa-2,5-diene-1,4-dione;
exhibited protection against LHON with an EC$_{50}$ of less than about 100 nM.

Example D

Screening Compounds of the Invention in Fibroblasts from Parkinson's Disease Patients Compounds of the invention were tested using a screen similar to the one described in Example A described in Example A, but substituting FRDA cells with Parkinson's Disease (PD) cells obtained from the Coriell Cell Repositories (Camden, N.J.; repository number AG20439). The compounds were tested for their ability to rescue human dermal fibroblasts from Parkinson's Disease patients from oxidative stress.

Certain compounds of the present invention such as:
2,3,5-trimethyl-6-(2-(pyrimidin-2-ylamino)ethyl)cyclohexa-2,5-diene-1,4-dione;

2,3,5-trimethyl-6-(2-(pyridin-2-ylamino)ethyl)cyclohexa-2,5-diene-1,4-dione;

2,3,5-trimethyl-6-(2-(4-(trifluoromethyl)pyrimidin-2-ylamino)ethyl)cyclohexa-2,5-diene-1,4-dione;

2,3,5-trimethyl-6-(2-(4-(trifluoromethyl)pyridin-2-ylamino)ethyl)cyclohexa-2,5-diene-1,4-dione;

2,3,5-trimethyl-6-(2-(5-(trifluoromethyl)pyridin-2-ylamino)ethyl)cyclohexa-2,5-diene-1,4-dione;

2,3,5-trimethyl-6-(2-(6-(trifluoromethyl)pyridin-2-ylamino)ethyl)cyclohexa-2,5-diene-1,4-dione;

2,3,5-trimethyl-6-(2-(3-(trifluoromethyl)pyridin-2-ylamino)ethyl)cyclohexa-2,5-diene-1,4-dione;

2-(2-(5-fluoropyrimidin-2-ylamino)ethyl)-3,5,6-trimethyl-cyclohexa-2,5-diene-1,4-dione; and 2-(2-(4-fluoropyrimidin-2-ylamino)ethyl)-3,5,6-trimethyl-cyclohexa-2,5-diene-1,4-dione;

exhibited protection against PD with an $EC_{50}$ of less than about 100 nM.

Example E

Screening Compounds of the Invention in Fibroblasts from CoQ10 Deficient Patients Compounds of the invention were tested using a screen similar to the one described in Example A, but substituting FRDA cells with cells obtained from CoQ10 deficient patients harboring a CoQ2 mutation. The compounds were tested for their ability to rescue human dermal fibroblasts from CoQ10 deficient patients from oxidative stress.

Certain compounds of the present invention such as:

2,3,5-trimethyl-6-(2-(pyrimidin-2-ylamino)ethyl)cyclohexa-2,5-diene-1,4-dione;

2,3,5-trimethyl-6-(2-(pyridin-2-ylamino)ethyl)cyclohexa-2,5-diene-1,4-dione;

2,3,5-trimethyl-6-(2-(4-(trifluoromethyl)pyrimidin-2-ylamino)ethyl)cyclohexa-2,5-diene-1,4-dione;

2,3,5-trimethyl-6-(2-(4-(trifluoromethyl)pyridin-2-ylamino)ethyl)cyclohexa-2,5-diene-1,4-dione;

2,3,5-trimethyl-6-(2-(5-(trifluoromethyl)pyridin-2-ylamino)ethyl)cyclohexa-2,5-diene-1,4-dione;

2,3,5-trimethyl-6-(2-(6-(trifluoromethyl)pyridin-2-ylamino)ethyl)cyclohexa-2,5-diene-1,4-dione;

2,3,5-trimethyl-6-(2-(3-(trifluoromethyl)pyridin-2-ylamino)ethyl)cyclohexa-2,5-diene-1,4-dione;

2-(2-(5-fluoropyrimidin-2-ylamino)ethyl)-3,5,6-trimethyl-cyclohexa-2,5-diene-1,4-dione; and 2-(2-(4-fluoropyrimidin-2-ylamino)ethyl)-3,5,6-trimethyl-cyclohexa-2,5-diene-1,4-dione;

exhibited protection against CoQ10 deficiency with an $EC_{50}$ of less than about 100 nM.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of Formula I

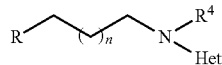

Formula I

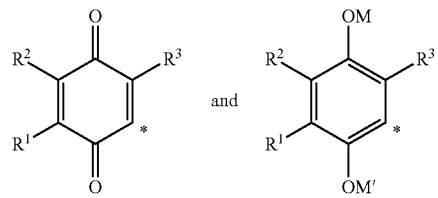

where R is selected from the group consisting of:

where the * indicates the point of attachment of R to the remainder of the molecule;

n is 0 or 1;

$R^1$ and $R^2$ are independently selected from the group consisting of hydrogen, $(C_1\text{-}C_6)$alkyl, and $(C_1\text{-}C_6)$alkoxy;

$R^3$ is $(C_1\text{-}C_6)$alkyl or $(C_1\text{-}C_6)$alkoxy;

$R^4$ is hydrogen, $(C_1\text{-}C_6)$alkyl, hydroxy, or $(C_1\text{-}C_6)$alkoxy;

Het is optionally substituted pyrimidine;

M and M' are independently selected from the group consisting of hydrogen, —C(O)—$R^{10}$, —C(O)($C_2$-$C_6$)-alkenyl, —C(O)($C_2$-$C_6$)-alkynyl, —C(O)-aryl, —C(O)-heterocyclyl, —C(O)O—$R^{10}$, —C(O)NR$^{10a}$R$^{10b}$, $SO_2OR^{10}$, —$SO_2$—$C_1$-$C_6$-alkyl, —$SO_2$—($C_1$-$C_6$)-haloalkyl, —$SO_2$-aryl, —$SO_2$—NR$^{10a}$R$^{10b}$, P(O)(OR$^{10a}$)(OR$^{10b}$) and C-linked amino acid or di-peptide; and $R^{10}$, $R^{10a}$, and $R^{10b}$ are independently hydrogen or ($C_1$-$C_6$)-alkyl optionally substituted with —OH, —NH$_2$, —NH($C_1$-$C_4$ alkyl), —N($C_1$-$C_4$ alkyl)$_2$, —C(O)OH, —C(O)O—($C_1$-$C_4$)-alkyl or halogen;

or a salt, a solvate, or a hydrate thereof.

2. The compound of claim 1, wherein the compound has the formula:

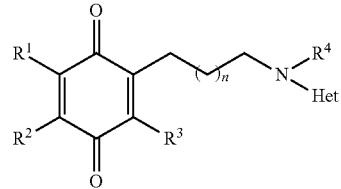

where:

n is 0 or 1;

$R^1$ and $R^2$ are independently selected from the group consisting of hydrogen, $(C_1\text{-}C_6)$alkyl, and $(C_1\text{-}C_6)$alkoxy;

$R^3$ is $(C_1\text{-}C_6)$alkyl or $(C_1\text{-}C_6)$alkoxy;

$R^4$ is hydrogen, $(C_1\text{-}C_6)$alkyl, hydroxy, or $(C_1\text{-}C_6)$alkoxy;

Het is pyrimidine optionally substituted with $(C_1\text{-}C_6)$alkyl, $(C_1\text{-}C_6)$haloalkyl, halogen, nitro, cyano, —C(O)($C_1$-$C_4$)alkyl, —C(O)($C_3$-$C_6$)cycloalkyl, —C(O)OH, —C(O)O($C_1$-$C_4$)-alkyl or oxo;

or a salt, a solvate, or a hydrate thereof.

3. The compound of claim 2, where n is 0.

4. The compound of claim 2 where $R^1$, $R^2$, and $R^3$ are independently $(C_1\text{-}C_4)$-alkyl.

5. The compound of claim 2 where $R^4$ is hydrogen.

6. The compound of claim 2 where Het is an unsubstituted pyrimidine.

7. The compound of claim 2, where Het is pyrimidine substituted with $(C_1-C_6)$alkyl, $(C_1-C_6)$haloalkyl, halogen, nitro, cyano, —C(O)$(C_1-C_4)$alkyl, —C(O)$(C_3-C_6)$cycloalkyl, —C(O)OH, —C(O)O$(C_1-C_4)$-alkyl or oxo.

8. The compound of claim 2, wherein the compound is selected from the group consisting of:
   2,3,5-trimethyl-6-(3-(pyrimidin-2-ylamino)propyl)cyclohexa-2,5-diene-1,4-dione;
   2,3,5-trimethyl-6-(2-(4-(trifluoromethyl)pyrimidin-2-ylamino)ethyl)cyclohexa-2,5-diene-1,4-dione;
   2-(2-(4-fluoropyrimidin-2-ylamino)ethyl)-3,5,6-trimethylcyclohexa-2,5-diene-1,4-dione;
   2-(2-(5-fluoropyrimidin-2-ylamino)ethyl)-3,5,6-trimethylcyclohexa-2,5-diene-1,4-dione; and
   2,3,5-trimethyl-6-(2-(pyrimidin-2-ylamino)ethyl)cyclohexa-2,5-diene-1,4-dione;
   or a salt, a solvate, or a hydrate thereof.

9. The compound of claim 2, additionally comprising a pharmaceutically acceptable excipient.

10. A method of treating or suppressing an oxidative stress disorder, comprising administering to a subject in need thereof a therapeutically effective amount of one or more compounds of claim 2, wherein the oxidative stress disorder is selected from the group consisting of Friedreich's Ataxia, Huntington's Disease, Leber's Hereditary Optic Neuropathy, Parkinson's Disease, diabetes, and CoQ10 deficiency.

11. The compound of claim 1, wherein the compound has the formula:

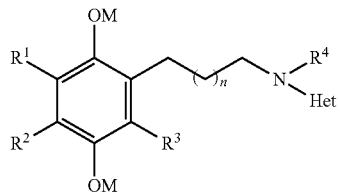

where:
n is 0 or 1;
$R^1$ and $R^2$ are independently selected from the group consisting of hydrogen, $(C_1-C_6)$alkyl, and $(C_1-C_6)$alkoxy;
$R^3$ is $(C_1-C_6)$alkyl or $(C_1-C_6)$alkoxy;
$R^4$ is hydrogen, $(C_1-C_6)$alkyl, hydroxy, or $(C_1-C_6)$alkoxy;
Het is pyrimidine optionally substituted with $(C_1-C_6)$alkyl, $(C_1-C_6)$haloalkyl, halogen, nitro, cyano, —C(O)$(C_1$-$C_4)$alkyl, —C(O)$(C_1$-$C_6)$cycloalkyl, —C(O)OH, —C(O)O$(C_1-C_4)$-alkyl or oxo;

M and M' are independently selected from the group consisting of hydrogen, —C(O)—$R^{10}$, —C(O)$(C_2-C_6)$-alkenyl, —C(O)$(C_2-C_6)$-alkynyl, —C(O)-aryl, —C(O)-heterocyclyl, —C(O)O—$R^{10}$, —C(O)$NR^{10a}R^{10b}$, $SO_2OR^{10}$, —$SO_2$—$C_1-C_6$-alkyl, —$SO_2$—$(C_1-C_6)$-haloalkyl, —$SO_2$-aryl, —$SO_2$—$NR^{10a}R^{10b}$, $P(O)(OR^{10a})(OR^{10b})$ and C-linked amino acid or di-peptide; and
$R^{10}$, $R^{10a}$, and $R^{10b}$ are independently hydrogen or $(C_1-C_6)$-alkyl optionally substituted with —OH, —$NH_2$, —$NH(C_1-C_4$ alkyl), —$N(C_1-C_4$ alkyl)$_2$, —C(O)OH, —C(O)O—$(C_1-C_4)$-alkyl or halogen;
or a salt, a solvate, or a hydrate thereof.

12. The compound of claim 11, where n is 0.

13. The compound of claim 11 where $R^1$, $R^2$, and $R^3$ are methyl and M and M' are independently hydrogen or C(O)—$R^{10}$.

14. The compound of claim 11, additionally comprising a pharmaceutically acceptable excipient.

15. A method of treating or suppressing an oxidative stress disorder; comprising administering to a subject in need thereof a therapeutically effective amount of one or more compounds of claim 11, wherein the oxidative stress disorder is selected from the group consisting of Friedreich's Ataxia, Huntington's Disease, Leber's Hereditary Optic Neuropathy, Parkinson's Disease, diabetes, and CoQ10 deficiency.

16. The compound of claim 11, wherein the compound is selected from the group consisting of:
   the hydroquinone form of 2,3,5-trimethyl-6-(3-(pyrimidin-2-ylamino)propyl)cyclohexa-2,5-diene-1,4-dione;
   the hydroquinone form of 2,3,5-trimethyl-6-(2-(4-(trifluoromethyl)pyrimidin-2-ylamino)ethyl)cyclohexa-2,5-diene-1,4-dione;
   the hydroquinone form of 2-(2-(4-fluoropyrimidin-2-ylamino)ethyl)-3,5,6-trimethylcyclohexa-2,5-diene-1,4-dione;
   the hydroquinone form of 2-(2-(5-fluoropyrimidin-2-ylamino)ethyl)-3,5,6-trimethylcyclohexa-2,5-diene-1,4-dione; and
   the hydroquinone form of 2,3,5-trimethyl-6-(2-(pyrimidin-2-ylamino)ethyl)cyclohexa-2,5-diene-1,4-dione;
   or a salt, a solvate, or a hydrate thereof.

17. A method of treating or suppressing an oxidative stress disorder, comprising administering to a subject in need thereof a therapeutically effective amount of one or more compounds of claim 1, wherein the oxidative stress disorder is selected from the group consisting of Friedreich's Ataxia, Huntington's Disease, Leber's Hereditary Optic Neuropathy, Parkinson's Disease, diabetes, and CoQ10 deficiency.

* * * * *